US012100141B2

(12) United States Patent
Tirupathi et al.

(10) Patent No.: US 12,100,141 B2
(45) Date of Patent: Sep. 24, 2024

(54) THREE-DIMENSIONAL DELINEATION OF TUMOR BOUNDARIES VIA SUPERVISED MACHINE LEARNING ALGORITHMS AND AUGMENTED REALITY

(71) Applicant: International Business Machines Corporation, Armonk, NY (US)

(72) Inventors: Seshu Tirupathi, Dublin (IE); Jonathan Peter Epperlein, Dublin (IE); Pol MacAonghusa, Carbury (IE); Rahul Nair, Dublin (IE); Tigran Tigran Tchrakian, Castleknock (IE); Mykhaylo Zayats, Dublin (IE); Sergiy Zhuk, Dublin (IE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 484 days.

(21) Appl. No.: 17/646,263

(22) Filed: Dec. 28, 2021

(65) Prior Publication Data

US 2023/0206431 A1 Jun. 29, 2023

(51) Int. Cl.
  *G06T 7/00* (2017.01)
  *A61B 5/00* (2006.01)
  (Continued)

(52) U.S. Cl.
  CPC .......... *G06T 7/0012* (2013.01); *A61B 5/0073* (2013.01); *G06T 19/006* (2013.01);
  (Continued)

(58) Field of Classification Search
  None
  See application file for complete search history.

(56) References Cited

U.S. PATENT DOCUMENTS 6,175,759 B1 *  1/2001  Chan ............... A61B 5/0091
                                                    600/431
6,785,409 B1    8/2004  Suri
                        (Continued)

FOREIGN PATENT DOCUMENTS

CN     107909102 A    4/2018
CN     113222903 A    8/2021
               (Continued)

OTHER PUBLICATIONS

International Search Report and Written Opinion received for PCT Application Serial No. PCT/CN2022/132211 dated Feb. 8, 2023, 10 pages.
(Continued)

*Primary Examiner* — Dov Popovici
(74) *Attorney, Agent, or Firm* — Amin, Turocy & Watson, LLP

(57) ABSTRACT

Techniques that facilitate three-dimensional (3D) delineation of tumor boundaries via one or more supervised machine learning algorithms are provided. An example embodiment includes a computer-implemented method that includes: extracting, by a computing system operatively coupled to a processor, one or more feature vectors from a time-series evolution of fluorescence distribution observed at a section of bodily tissue of interest, wherein the one or more feature vectors represent a physical model describing on-tissue dye dynamics of the section of bodily tissue; and generating, by the computing system, a classification attribute for the section of bodily tissue represented by the one or more feature vectors, wherein a pre-trained classifier designates the section of bodily tissue as a biopsy or a non-biopsy candidate through execution of the one or more supervised machine learning algorithms.

23 Claims, 19 Drawing Sheets
(5 of 19 Drawing Sheet(s) Filed in Color)

(51) Int. Cl.
*G06T 19/00* (2011.01)
*G16H 30/40* (2018.01)
*G16H 50/20* (2018.01)

(52) U.S. Cl.
CPC ............. *G16H 30/40* (2018.01); *G16H 50/20* (2018.01); *G06T 2207/30024* (2013.01)

(56) References Cited

U.S. PATENT DOCUMENTS

| | | | |
|---|---|---|---|
| 9,848,843 | B2 | 12/2017 | Grass et al. |
| 9,892,513 | B2 | 2/2018 | Gurevich et al. |
| 2011/0301447 | A1 | 12/2011 | Park et al. |
| 2017/0084024 | A1 | 3/2017 | Gurevich |
| 2017/0357844 | A1 | 12/2017 | Comaniciu et al. |
| 2017/0367580 | A1 | 12/2017 | DiMaio et al. |
| 2018/0028079 | A1 | 2/2018 | Gurevich et al. |
| 2018/0093030 | A1 | 4/2018 | Hestekin et al. |
| 2018/0130207 | A1 | 5/2018 | Anderson et al. |
| 2020/0342587 | A1 | 10/2020 | Epperlein et al. |
| 2021/0065372 | A1 | 3/2021 | Zhuk et al. |
| 2021/0249118 | A1* | 8/2021 | Papagiannakis ....... G16H 50/30 |

FOREIGN PATENT DOCUMENTS

| | | |
|---|---|---|
| CN | 113832211 A | 12/2021 |
| WO | 2018075679 A1 | 4/2018 |

OTHER PUBLICATIONS

Zhuk, et al., "Perfusion Quantification from Endoscopic Videos: Learning to Read Tumour Signatures," arXiv:2006.14321v1 [eess.IV] Jun. 25, 2020.

R. Cahill, et al., "Artificial intelligence indocyanine green (ICG) perfusion for colorectal cancer intra-operative tissue classification," British Journal of Surgery, vol. 108, No. 1, pp. 5-9, Jan. 1, 2021.

Halicek, et al., "In-Vivo and Ex-Vivo Tissue Analysis through Hyperspectral Imaging Techniques: Revealing the Invisible Features of Cancer," Cancers 2019, 11, 756; doi:10.3390/cancers11060756.

Hohmann, et al., "In-vivo multispectral video endoscopy towards in-vivo hyperspectral video endoscopy," J. Biophotonics 10, 553-564 (2017) / DOI 10.1002/jbio.201600021.

Lee, et al., "Design and Testing of Augmented Reality-Based Fluorescence Imaging Goggle for Intraoperative Imaging-Guided Surgery," Diagnostics 2021, 11, 927. https://doi.org/10.3390/diagnostics11060927.

Valdes, et al., "Optical technologies for intraoperative neurosurgical guidance," Neurosurg Focus. Mar. 2016 ; 40 (3): E8. doi:10.3171/2015.12.FOCUS15550.

Choi, Myunghwan, et al., "Dynamic fluorescence imaging for multiparametric measurement of tumor vasculature." Journal of Biomedical Optics 16(4), 046008 (Apr. 4, 2011).

Son, Gyung Mo, et al., "Quantitative analysis of colon perfusion pattern using indocyanine green (ICG) angiography in laparoscopic colorectal surgery." Surg Endosc May 2019;33(5):1640-1649. doi: 10.1007/s00464-018-6439-y. Epub Sep. 10, 2018.

J. Epperlein and S. Zhuk, "Biophysics-Inspired AI Uses Photons to Help Surgeons Identify Cancer" https://www.ibm.com/blogs/research/2019/02/biophysics-inspired-ai/, IBM Research Blog, Feb. 28, 2019.

Gurfinkel et al., "Pharmacokinetics of ICG and HPPH-car for the Detection of Normal and Tumor Tissue Using Fluorescence, Near-infrared Reflectance Imaging: A Case Study" Photochem Photobiol, Jul. 2000; 72(1):94-102. doi: 10.1562/0031-8655(2000)072<0094:poiahc>2.0.co;2.

Khokhar et al., "Illuminating neoplasia with systemic indocyanine green and near-infrared endoscopic system-clinical experience" vol. 2 (Feb. 2018) / AB027. 172., doi: 10.21037/map.2018.AB027.

Thatcher et al., "Imaging Techniques for Clinical Burn Assessment with a Focus on Multispectral Imaging," Adv Wound Care (New Rochelle). Aug. 1, 2016; 5(8): 360-378., Published online Aug. 1, 2016. doi: 10.1089/wound.2015.0684.

Mell et al., "The NIST Definition of Cloud Computing," Recommendations of the National Institute of Standards and Technology, NIST Special Publication 800-145, Sep. 2011, 7 pages.

* cited by examiner

EMBODIMENT 1 – LIVE TUMOR BOUNDARY DELINEATION IN COLORECTAL SURGERY

DYE ADMINISTRATION AND MULTISPECTRAL VIDEO GENERATION- NOT PART OF INVENTION
1100

TRACKING COMPONENT

1202

INVERSION AND TISSUE CLASSIFICATION COMPONENT     1204

THREE-DIMENSIONAL DELINEATION OF TUMOR BOUNDARIES VIA SUPERVISED MACHINE LEARNING ALGORITHMS AND AUGMENTED REALITY

BACKGROUND

The subject disclosure relates to three-dimensional (3D) delineation of tumor boundaries via supervised machine learning algorithms and augmented reality (AR).

SUMMARY

The following presents a summary to provide a basic understanding of one or more embodiments of the invention. This summary is not intended to identify key or critical elements or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus, and/or computer program products that facilitate 3D delineation of tumor boundaries via supervised machine learning algorithms and AR.

An embodiment includes a computer-implemented method. The computer-implemented method comprises extracting, by a computing system operatively coupled to a processor, one or more feature vectors from a time-series evolution of fluorescence distribution observed at a section of bodily tissue of interest, wherein the one or more feature vectors represent a physical model describing on-tissue dye dynamics of the section of bodily tissue. The computer-implemented method also comprises generating, by the computing system, a classification attribute for the section of bodily tissue represented by the one or more feature vectors, wherein a pre-trained classifier designates the section of bodily tissue as a biopsy or a non-biopsy candidate through execution of one or more supervised machine learning algorithms.

Another embodiment includes a system, comprising: a memory; and a processor that executes computer-executable components stored in the memory. The computer-executable components comprise: a feature composition component that extracts one or more feature vectors from a time-series evolution of fluorescence distribution observed at a section of bodily tissue of interest, wherein the one or more feature vectors represent a physical model describing on-tissue dye dynamics of the section of bodily tissue; and a classification component of a pre-trained classifier, wherein the classification component generates a classification attribute for the section of bodily tissue represented by the one or more feature vectors, and wherein the pre-trained classifier designates the section of bodily tissue as a biopsy or a non-biopsy candidate through execution of one or more supervised machine learning algorithms.

Another embodiment includes a computer-implemented method. The computer-implemented method comprises: analyzing, by a computing system operatively coupled to a processor, one or more inputs in the form of multispectral videos representative of on-tissue dye dynamics at a section of bodily tissue of interest; and generating, by the computing system, a mesh representing one or more absorption coefficients at different times and a description of one or more geometric boundaries of the section of bodily tissue, wherein the outputting is based on the analyzing. The computer-implemented method also comprises training, by the computing system, a classification component of the computing system through supervised machine learning algorithms to classify a particular group of one or more feature vectors of the section of bodily tissue of interest as biopsy candidates or non-biopsy candidates.

Another embodiment includes a system comprising: a memory; and a processor that executes computer-executable components stored in the memory. The computer-executable components comprise: a classification component that: analyzes multispectral video having one or more voxels, wherein the multispectral video is generated by a medical imaging device; and generates a classification of bodily tissue that is visible or invisible in the multispectral video generated by the medical imaging device, wherein the classification is provided for the one or more voxels, and wherein the classification also comprises a value indicating a confidence that the classification is accurate as applied to the one or more voxels.

DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
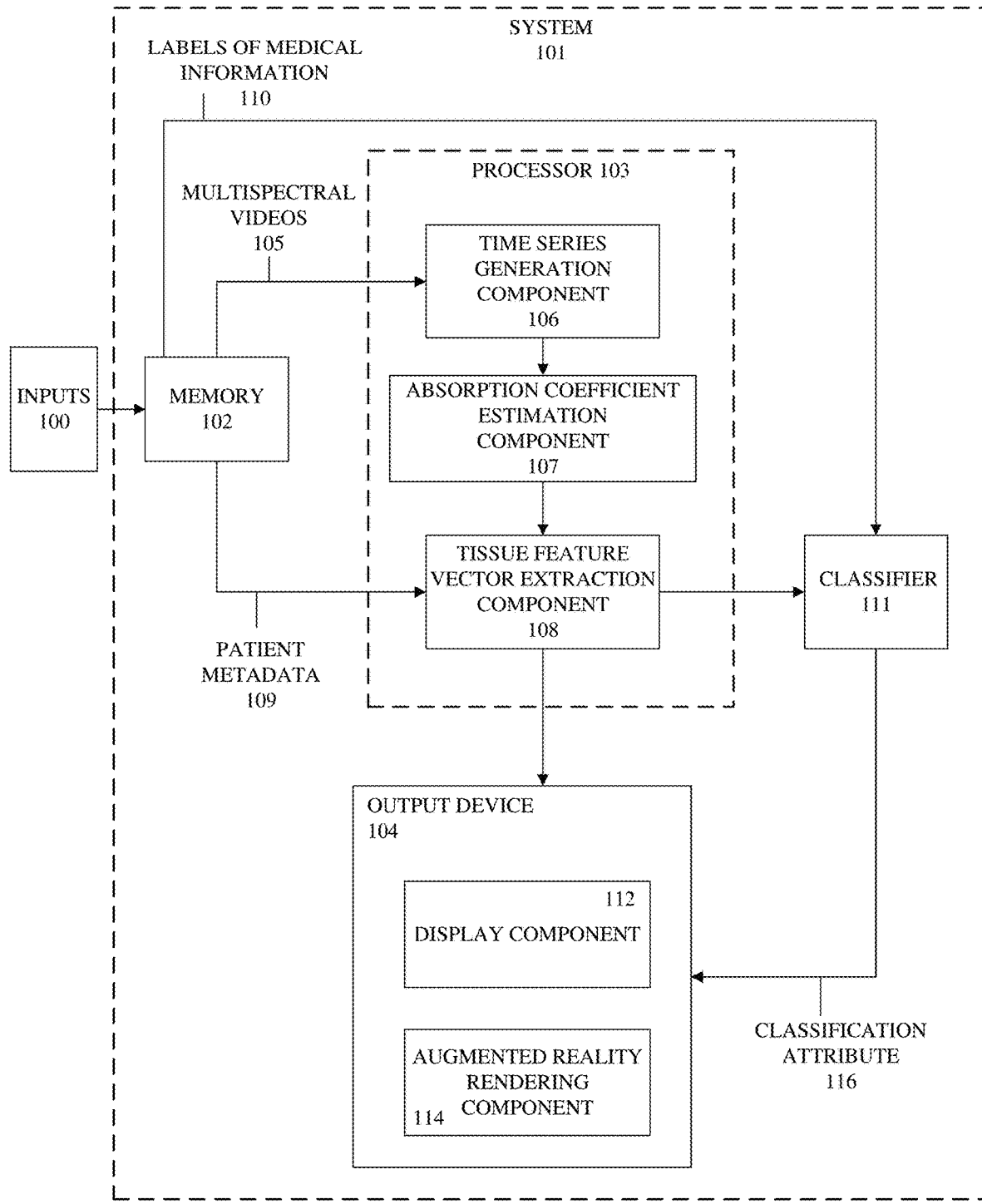
FIG. 1 illustrates a block diagram of an example, non-limiting computer-implemented system and environment that facilitates diagnosis of a section of bodily tissue in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

The various embodiments described herein can relate to 3D delineation of tumor boundaries via supervised machine learning algorithms and AR. The various embodiments and configurations offer a non-invasive way for medical experts and doctors to infer physical characteristics of unseen tissue beneath the surface of the visible region. Initially, a dye can be administered at the section of bodily tissue to generate fluorescence. Monitoring the fluorescence can generate information about one or more sections of the tissue and the information can be recorded for further analysis and generation of a classification attribute and a three-dimensional bio-physical model for the tissue. The classification attribute can be determined in one or more embodiments herein. For example, the classification attribute and bio-physical augmented reality model determined/generated in one or more embodiments can be output from a device and evaluated by the clinical doctor in some embodiments. Further, based on this process, the clinical doctor may determine that ordering additional tests, performing surgery, or taking another approach is warranted. In some embodiments, the classification, uncertainty score and/or augmented reality display of the delineated tumor can control one or more subsequent actions. For example, the one or more subsequent actions can be or include triggering of automated ordering of additional patient tests via transmitting a signal and/or the classification attribute, uncertainty scores and/or augmented reality display via one or more computer networks.

The above-described approach of the one or more embodiments herein can lead to an accurate diagnosis of the underlying conditions. Further, in one or more of the embodiments described herein, automating the process of understanding 3D, tomographic tissue structure based on its perfusive properties can lead to one or more advantages including, but not limited to, less experienced surgeons can look to the system based on the knowledge of many experts for guidance; finely meshed three-dimensional assessments can be used to delineate cancerous tissue on, and under, the visible region of tissue to further guide resection decisions; if the assessments of such a process are confident enough, biopsies and pathologist evaluation can be skipped, offering a diagnosis in almost real time; and/or a robotic surgeon can be set to resect tissue which is classified as cancerous, requiring surgeons to supervise, but not to perform the operation directly.

One or more embodiments described herein can provide a system to detect regions of bodily tissue captured in multispectral video stream(s) with distinct light absorption patterns representing blood perfusion in the tissue and delineate their geometric boundaries in three spatial dimensions; classify the perfusion patterns of the regions of a tissue into medically meaningful classes; and/or generate or improve such a classifier from a dataset of such multispectral videos streams, labeled with medically meaningful labels. One or more embodiments employ real-time tracking of tissue in multispectral videos; a bio-physical model or models of light propagation in three spatial dimensions; one or more algorithms that estimate absorption and scattering coefficients of light propagation model in biological tissue; and/or supervised machine learning/classification algorithms.

The principal challenge addressed by the invention is that it can provide a real-time, in-vivo digital biopsy capability wherein tissue can be classified into clinically meaningful categories (for example, healthy, benign, cancerous) without needing to remove the tissue and send for subsequent pathological analysis. This capability can augment the decision making of the surgical team, improve the accuracy of tissue removal during surgery, and reduce the uncertainty due to current waiting times for pathological follow up.

FIG. 1 illustrates a block diagram of an example, non-limiting computer-implemented system and environment that facilitates diagnosis of a section of bodily tissue in accordance with one or more embodiments described herein. Fluorescent dyes can be used in many surgical domains by administration of dye to a patient. The dye is transported through the body of the patient via the blood stream, which is the perfusion process. The presence of the dye in a segment of bodily tissue can lead to fluorescence of light at a certain wavelength when the light is shone onto the tissue wherein light at certain different wavelengths can be emitted from the bodily tissue. Light propagation through bodily tissue as a function of tissue optical properties (e.g., absorption and scattering) can be described by photon diffusion equations. In various embodiments of the invention described herein, by observing values of fluorescence intensities over time, parameters of the photon diffusion equations can be reconstructed and applied to infer characteristics of unseen tissue lying beneath the surface of the visible region. Such a tomographic (i.e., 3D) augmented reality reconstruction of tissue properties in one or more embodiments herein can be output. Further, this reconstruction can facilitate a non-invasive approach to allowing a medical expert to understand properties of tissue on, and beneath, the visible surface. For example, in one or more embodiments described herein, it has been observed that cancerous tissue usually retains dye much longer than healthy tissue does (hours vs 15-20 min) and results in different values of reconstructed optical properties. Bounds of error are used to inform the viewer of the degree of confidence of the 3D tomographic reconstruction. An objective, quantitative way of presenting 3D information, automatically derived from time-series of the fluorescence intensity profiles can inform the decision making of medical experts, improve individual decision making by giving access to decision making of the expert community, and/or enable automation of surgical intervention. In one or more embodiments, characterizing the bodily tissue over time through an automated approach can enable tracking of the behaviour of several regions on a timescale of seconds or less. The various embodiments herein do not require human observation of the long, almost stationary phase during which the dye persists in the cancer but has been washed out from the healthy tissue to determine characteristics of the bodily tissue.

Turning now to FIG. 1, a computer system represented by system 101 coupled to a processor 103 can generate a classification attribute 116 that can be later used in a clinical environment where an output device 104 can be located. In some embodiments, the classification attribute 116 can be generated within a facility such as a medical research facility, while in other embodiments the prediction model can be generated within hospitals, clinics, or medical testing laboratories. The system 101 can include a memory 102, a time series generation component 106, an absorption coefficient estimation component 107, a tissue feature vector extraction component 108 and a classifier 111. The classification attribute 116 can be generated by information analyzed by the classifier from the time series generation component 106, the absorption coefficient estimation component 107, and the tissue feature vector extraction component 108. The classifier can consist of one or more supervised machine learning algorithms that generate a model that assigns labels and/or attributes to the feature vectors representing the section of bodily tissue. The classifier can be trained to distinguish tissue categories using a collection of labelled prior examples of the one or more tissue feature vectors extracted by the tissue feature vector extraction component 108. Once trained, the classifier can generalize to assign labels and/or attributes to the feature vectors representing a section of previously unseen bodily tissue. In the classification process, a medical expert, such as a surgeon, can identify clinically relevant categories or labels of human tissue, including healthy, benign, and cancerous. Categories or labels can be deemed medically meaningful in the sense that distinguishing tissues of different types can be relevant to the performance of a medical procedure. For example, a surgeon can seek to minimize removal of healthy tissue, while endeavoring to remove as much cancerous and benign tissue as possible. During the classifier training process, examples of previous procedures can be annotated by expert users to mark regions containing tissue of particular types represented by the expert-defined categories or labels. Annotation can be performed by annotating still images taken from one or more multispectral videos 105 of a previous procedure, for example. Annotated still images can be used to identify and subsequently track regions of different tissue categories or labels while extracting and estimating tissue characteristics including time-series, absorption coefficients and feature vectors representing on-tissue dye-dynamics. This can then be combined with patient metadata and labels of medical information and input to the classifier 111 as training data.

The memory 102 can collect/receive input data from inputs block 100, and then can format, organize, and store the input data by employing algorithms programmed to sort data. From the collected data, inputs in the form of one or more multispectral videos 105 can be passed to the time series generation component 106, wherein the input data can be further analyzed by the processor to extract a different set of information. This new set of information generated by block 106 can be passed onto the absorption coefficient estimation component 107 where it can be parametrized using one or more estimation algorithms. Component 107 can take the time-series extracted by component 106 and can employ estimation algorithms to produce an estimate of the absorption coefficient of the tissue contained in the region corresponding to the extracted time-series. The estimation algorithms can comprise a mathematical process called inversion of differential equations during which observed data, such as the time-series extracted by component 106, can be used to invert one or more Diffuse Optical Tomography (DOT) equations by selecting the values of the absorption coefficient in the DOT equation that best match the observed data. Adjoint methods are one example of such a mathematical technique that can be used for DOT equation inversions. The estimated absorption coefficient parameters generated in block 107 can then be passed on to the tissue feature vector extraction component 108 for correlation with inputs of patient metadata 109 stored in memory 102, which can generate feature vector information about the section of bodily tissue. Together with inputs of labels of medical information 110 from memory 102, the feature vector information can be combined in the classifier 111 to generate the classification attribute 116 based on the correlation results such that it can be further used to diagnose new and different patients. Herein, correlation can refer to the agreement with the internal representation of the feature space learned by the classifier 111. Given a new, unseen example, described by features generated by components 107 through 109, the classifier 111 can assign one or more labels to one or more feature vectors by choosing labels whose features can be a best match for the unseen example. The exact method to identify a best match between features can be a function of the machine learning model selected and the setting of its internal parameters. During the training phase, the classifier can be trained to choose the appropriate machine learning algorithm and the values of its parameters. The classification attribute 116 generated by the classifier 111 can be output onto the output device 104 for viewing and further analysis.

The output device 104 can be located at a clinical office or a facility of similar capacity remote to the system 101 where the classification attribute 116 was produced, or it can be part of the system 101. The output device 104 is represented by a display component 112 and an augmented reality rendering component 114. The classification attribute 116 can produce a diagnosis which can further generate, format, and/or output information and 3D parametric models using the augmented reality rendering component 114. The output information and 3D models can be displayed on one or more output devices such as output device 104 using the display component 112.

Thus, an environment similar to that of FIG. 1 can use input information in the form of patient metadata and retrieve fluorescence profiles generated at the section of bodily tissue to generate a predictive model of the tissue and its boundaries such that the tissue can be further diagnosed and classified as a biopsy or a non-biopsy candidate. The system 101 can provide medically meaningful classifications of living tissue by receiving a database of multispectral intraoperative videos such that each element of the database has zero or more rows of patient metadata and some elements of the database have one or more medically meaningful labels. The system 101 can also provide a classification for some or all tissue that are visible or invisible in a provided video such that the classification for each voxel is a number indicating a confidence score that describes if the classification is applicable for the voxel it is applied to.

Figure 2:
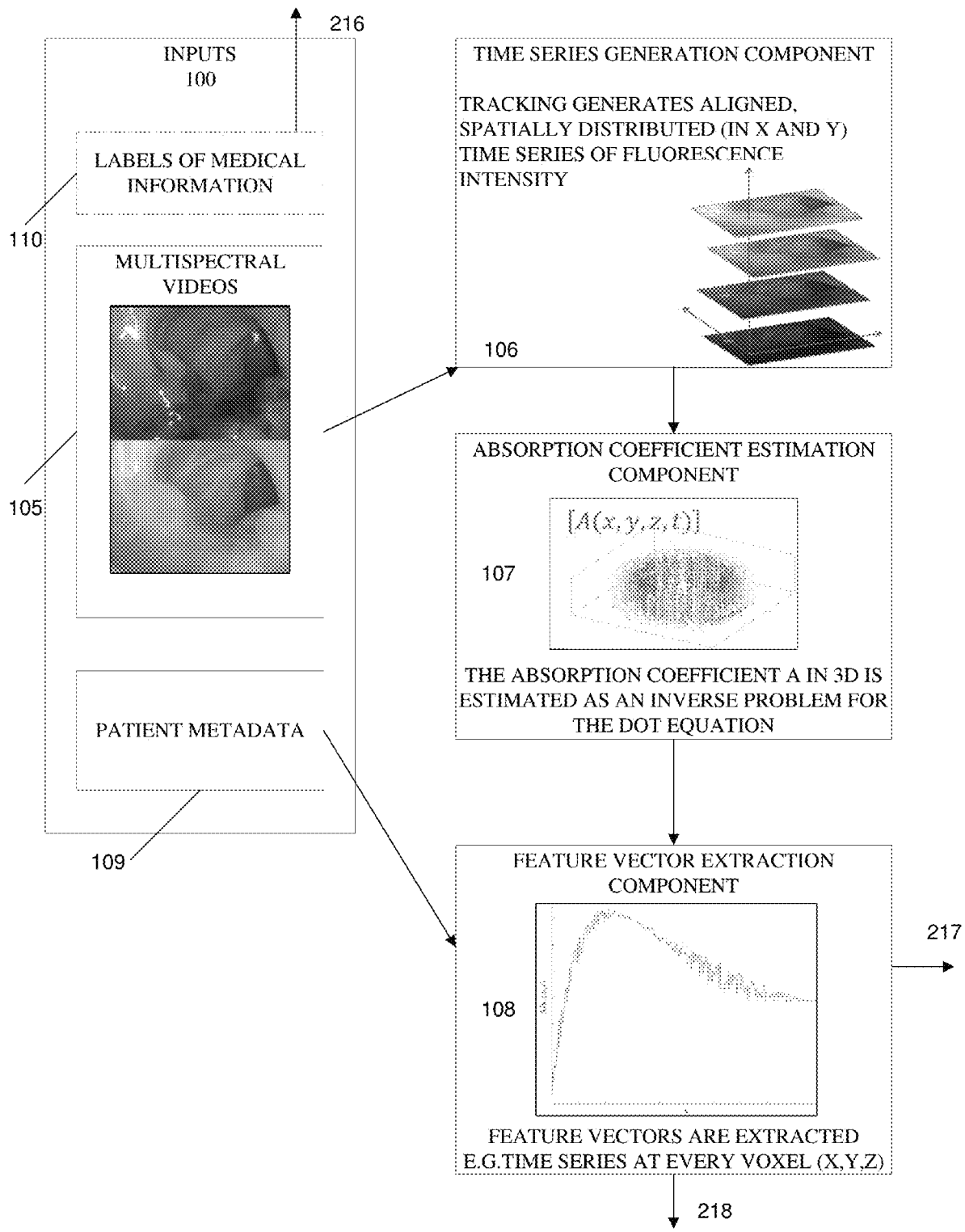
FIG. 2 illustrates a block diagram of an example, non-limiting computer-implemented system that elaborates on the input-output flow of data that facilitates diagnosis of the section of bodily tissue as described by the system discussed with reference to FIG. 1.

FIG. 2 illustrates a block diagram of an example, non-limiting computer-implemented system that elaborates on the input-output flow of data that facilitates diagnosis of the section of bodily tissue as described by the system discussed with reference to FIG. 1. The set of inputs 100 comprises data received by the memory 102 which can include labels of medical information 110, multispectral videos 105, and patient metadata 109. The block diagram also comprises the time series generation component 106, absorption coefficient estimation component 107, and tissue feature vector extraction component 108 of FIG. 1. Channels 216, 217 and 218 can represent information which can be passed onto other components from inputs block 100 and components 106, 107 and 108.

Time series generation component 106 can receive multispectral videos 105 stored in the memory 102 of FIG. 1 and can analyze them via a processor to extract and record time-series of fluorescence emitted by the section of bodily tissue resulting from on-tissue dye dynamics. Recording is based on real-time tracking of tissue movement, in a coordinate system fixed to the patient, resulting in spatially distributed two-dimensional (2D) time series of fluorescence. The recorded time-series can be stored on a storage component of the computer system wherein the storage component can be a hard drive internal or external to the computer device. If the data is stored internally within the computer device, it can be stored within the memory 102 of FIG. 1.

Recorded time-series of fluorescence intensities from the time-series generation component 106 can be further analyzed by the absorption coefficient estimation component 107 of the computer system wherein the processor of the computing system can use estimating algorithms, as described in one or more embodiments herein, to estimate absorption coefficients of the time-series as an inverse problem for DOT equations. The absorption coefficients are a mathematical representation of the on-tissue dye dynamics at the section of bodily tissue. The computer can represent the dye dynamics in 3D space using the DOT equations, thereby delineating the tumor boundaries. As discussed earlier, parametrization from the absorption coefficient estimation component 107 can be used in conjunction with patient metadata 109 to extract feature vectors of the time-series of absorption by the feature vector extraction component 108 of the computer system. The data recorded and analyzed thus far can be communicated via channels 216, 217, 218 for further classification and diagnosis which is discussed in successive figures.

Figure 3:
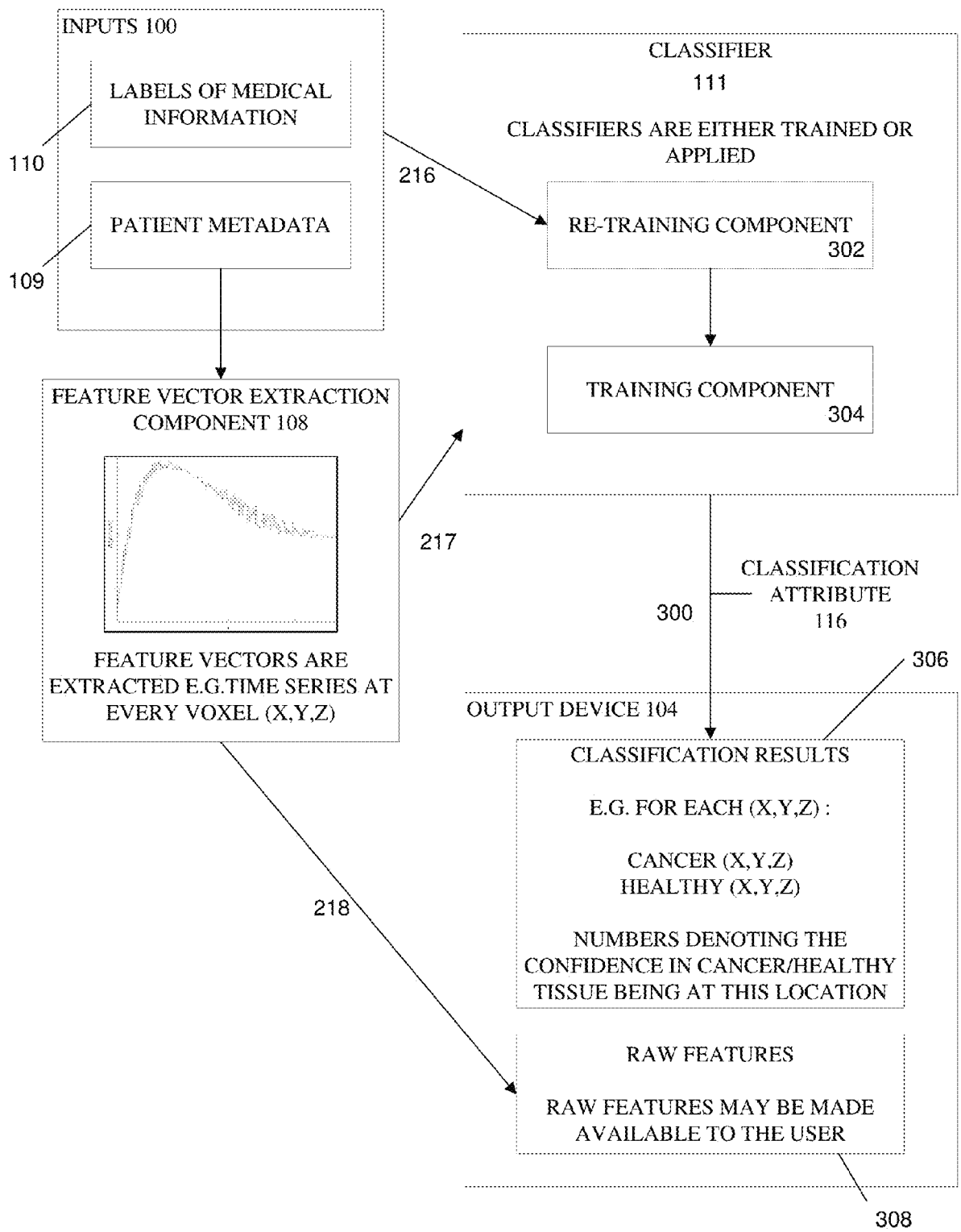
FIG. 3 illustrates a block diagram of an example, non-limiting computer-implemented system that elaborates on the input-output flow of data that facilitates diagnosis of the section of bodily tissue as described by the system discussed with reference to FIG. 1.

FIG. 3 illustrates a block diagram of an example, non-limiting computer-implemented system that elaborates on the input-output flow of data that facilitates diagnosis of the section of bodily tissue as described by the system discussed with reference to FIG. 1. The block diagram comprises inputs block 100 comprising labels of medical information 110 and patient metadata 109, feature vector extraction component 108, classifier 111, classification attribute 116 and output device 104 of FIG. 1, and communication lines 216, 217, and 218 of FIG. 2. Classifier 111 can include re-training component 302 and training component 304. Output device 104 can include classification results 306 and raw features 308.

The training component 304 can receive inputs of one or more feature vectors from feature vector extraction component 108 to train the classifier 111 within the computer system to assign labels of medical information stored in memory to feature vectors representing the section of bodily tissue. The re-training component 302 can receive inputs of one or more labels of medical information 110 as well as one or more feature vectors from feature vector extraction component 108. The re-training component 302 can process new data generated by the trained classifier to increase the accuracy of the classifier. The classifier 111 can be one or more supervised machine learning algorithms which rely on multiple prediction models to apply appropriate labels to the section of bodily tissue and apply confidence scores describing the accuracy of the applied labels. Random Forest classifier is an example. The classifier can be employed within the primary computer in accordance with one or more embodiments described here, or it could be employed within a separate set of hardware that is part of the computing system as a whole.

Input lines 216 and 217 can contain one or more communication lines that provide medical data associated with a patient and feature vector information representing on-tissue dye dynamics at the section of bodily tissue, into the classifier 111. An output line 300 can contain one or more individual output lines to bring signal(s) specifying the classification attribute 116 generated by the classifier 111 to output device 104. Additional data that can be received by output device 104 can include classification results 306 and raw features in the form of one or more feature vectors from feature vector extraction component 108. These outputs can be used by other devices to predict future medical conditions. The input lines 216, 217 and 218 and output line 300 can be single lines or multiple lines/busses and can be part of the computer system coupled with the processor or can be communicatively, removably attached to the computer system (or device ports). As addressed in embodiments described herein, the computer system generates various outputs for the section of bodily tissue. These outputs can be made available on various output devices and removable/non-removable interfaces as well as in the form of augmented reality (AR) view wherein the augmented reality view can comprise assigning a color corresponding to one or more labels assigned to the section of bodily tissue during classification. For example, cancerous tissue can be denoted as red, healthy tissue as green and benign tissue as orange. Colors can also be chosen by a user. The system can display a visual overlay of the tissue by assigning the appropriate color to regions of the corresponding tissue type. The created overlay can be merged with the streamed video to create a color-augmented view of the underlying tissue, highlighting regions of various tissue types.

The geometric representation of the tissue along with a percentile accuracy score for assigned labels can be presented to a domain expert via a portable hard drive before surgery for further diagnosis. Concurrently, the same data can be displayed as active feed on a different device such as virtual reality goggles during an active surgery. A mesh representing absorption coefficient geometry at any given time stamp of fluorescence can also be stored in the computer memory and shared with the user over a hard drive as a raw feature for analysis. New output data that maybe used for re-training a classifier can be uploaded to overwrite pre-existing outdated information in the storage component of the computer system.

Figure 4:
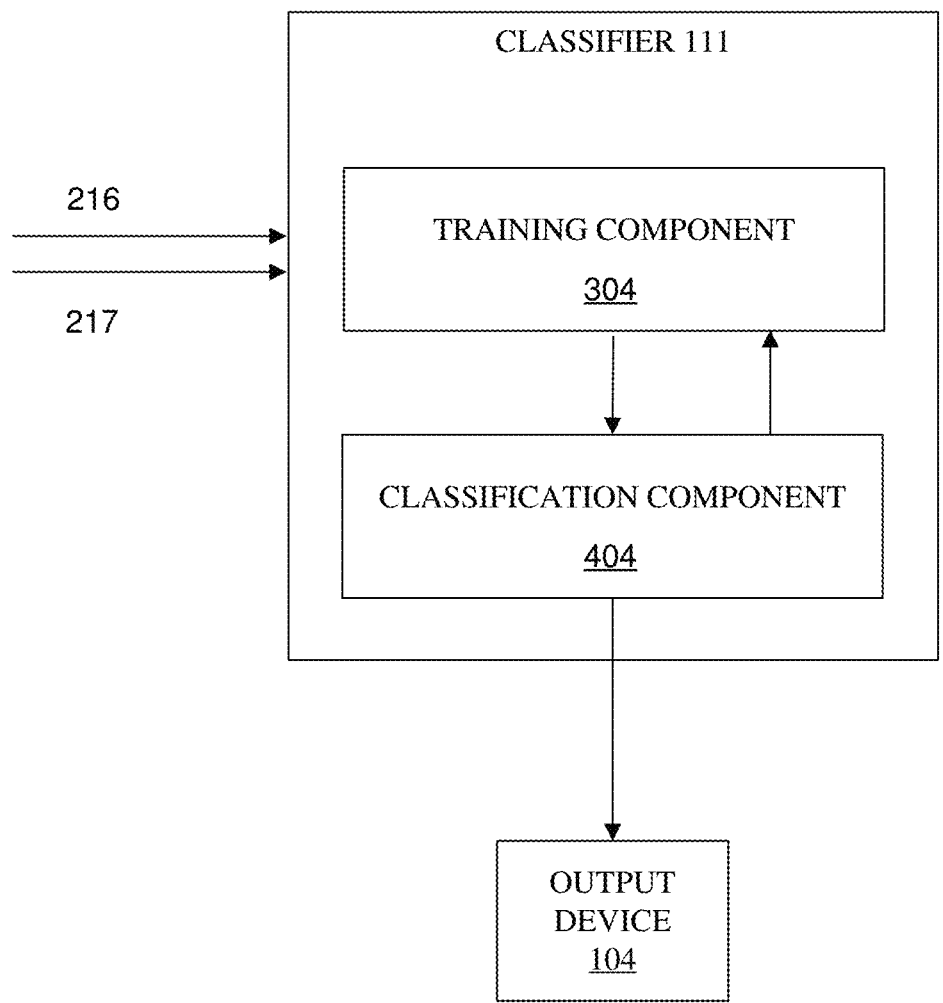
FIG. 4 illustrates a block diagram of an example, non-limiting computer-implemented system that elaborates on the classification component of the input-output flow of data as described with reference to FIG. 3.

FIG. 4 illustrates a block diagram of an example, non-limiting computer-implemented system that elaborates on the classification component of the input-output flow of data as described with reference to FIG. 3. The block diagram comprises classifier 111, and output device 104 of FIG. 1 and communication channels 216, 217, and 218 of FIG. 2.

Classifier 111 can include classification component 404 in addition to training component 304. The training component 304 can receive inputs used to train the classification component 404 of the classifier 111 within the computer system. The classifier 111 can be a set of supervised machine learning algorithms that act as a model to assign labels and attributes to the feature vectors representing the section of bodily tissue through its classification component 404 which uses input data to identify similarities in conditions represented by the tissue and by characteristics of similar conditions available for reference as inputs. The training component 304 and classification component 404 can communicate new data and feedback amongst each other to increase the accuracy of the classification model via machine learning algorithms.

Figure 5:
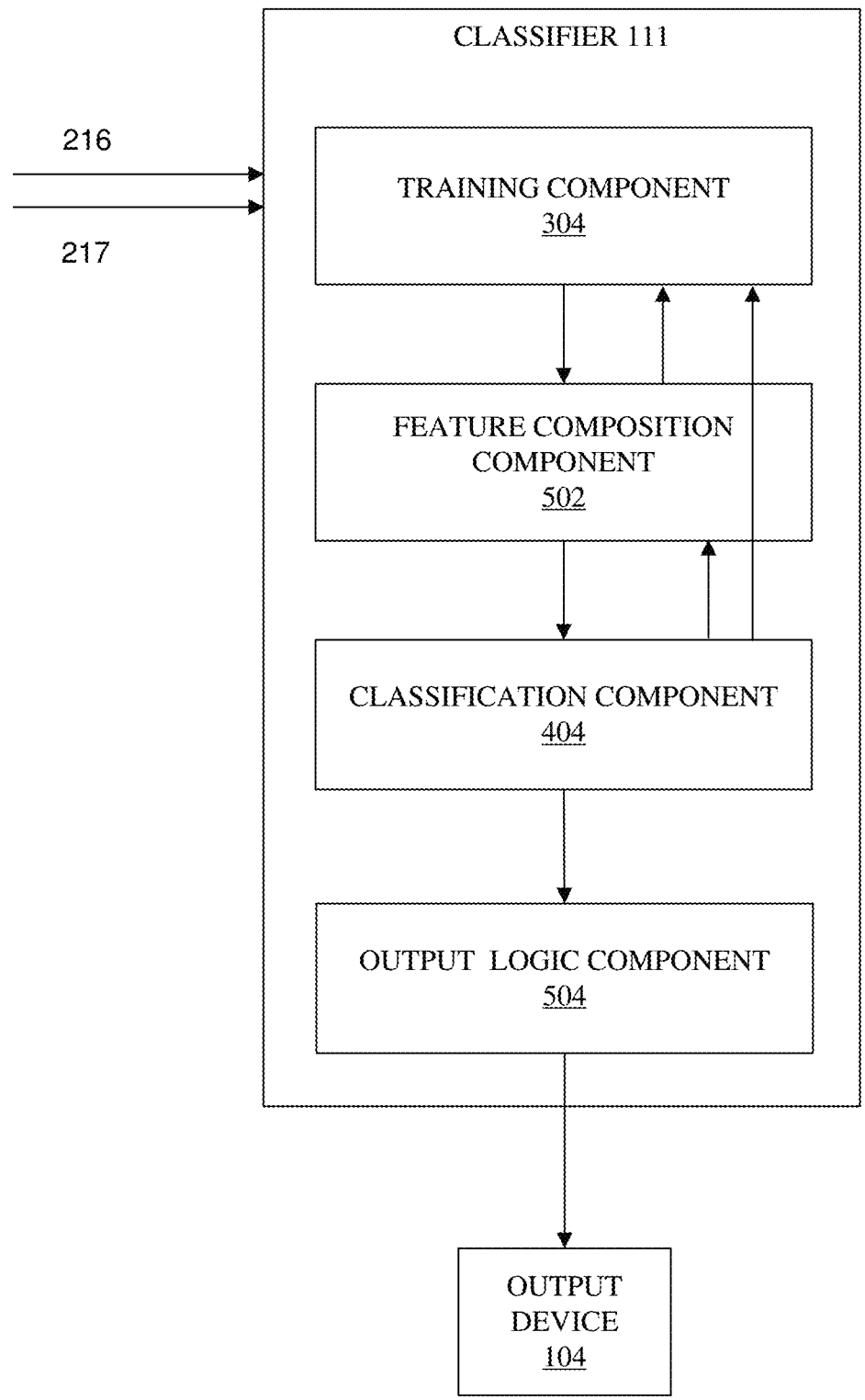
FIG. 5 illustrates another block diagram of an example, non-limiting computer-implemented system that elaborates on the classification component of the input-output flow of data as described with reference to FIG. 3.

FIG. 5 illustrates a block diagram of an example, non-limiting computer-implemented system that elaborates on the classification component of the input-output flow of data as described with reference to FIG. 3. The block diagram comprises classifier 111, and output device 104 of FIG. 1, communication channels 216, 217, and 218 of FIG. 2, training component 304 of FIG. 3 and classification component 404 of FIG. 4.

Classifier 111 can include feature composition component 502 and output logic component 504 in addition to training component 304 and classification component 404. Repetitive description of like elements employed in other embodiments described herein is omitted for sake of brevity. The feature composition component 502 can function as part of the feedback algorithm that trains and re-trains the classification component to improve classification accuracy. A well-trained feature composition component can generate a more accurate and precise description of the feature vectors, and therefore, of the on-tissue dye dynamics (which can be beneficial as the time-series extraction is based on real-time tracking of fluorescence and tissue movement, and geometric accuracy regarding the coordinate system is valuable).

The classifier 111 can further include an output logic component 504 that can output the revised prediction model for use by other medical devices to generate a more detailed medical diagnosis based on the image and meta data of the patient.

Figure 6:
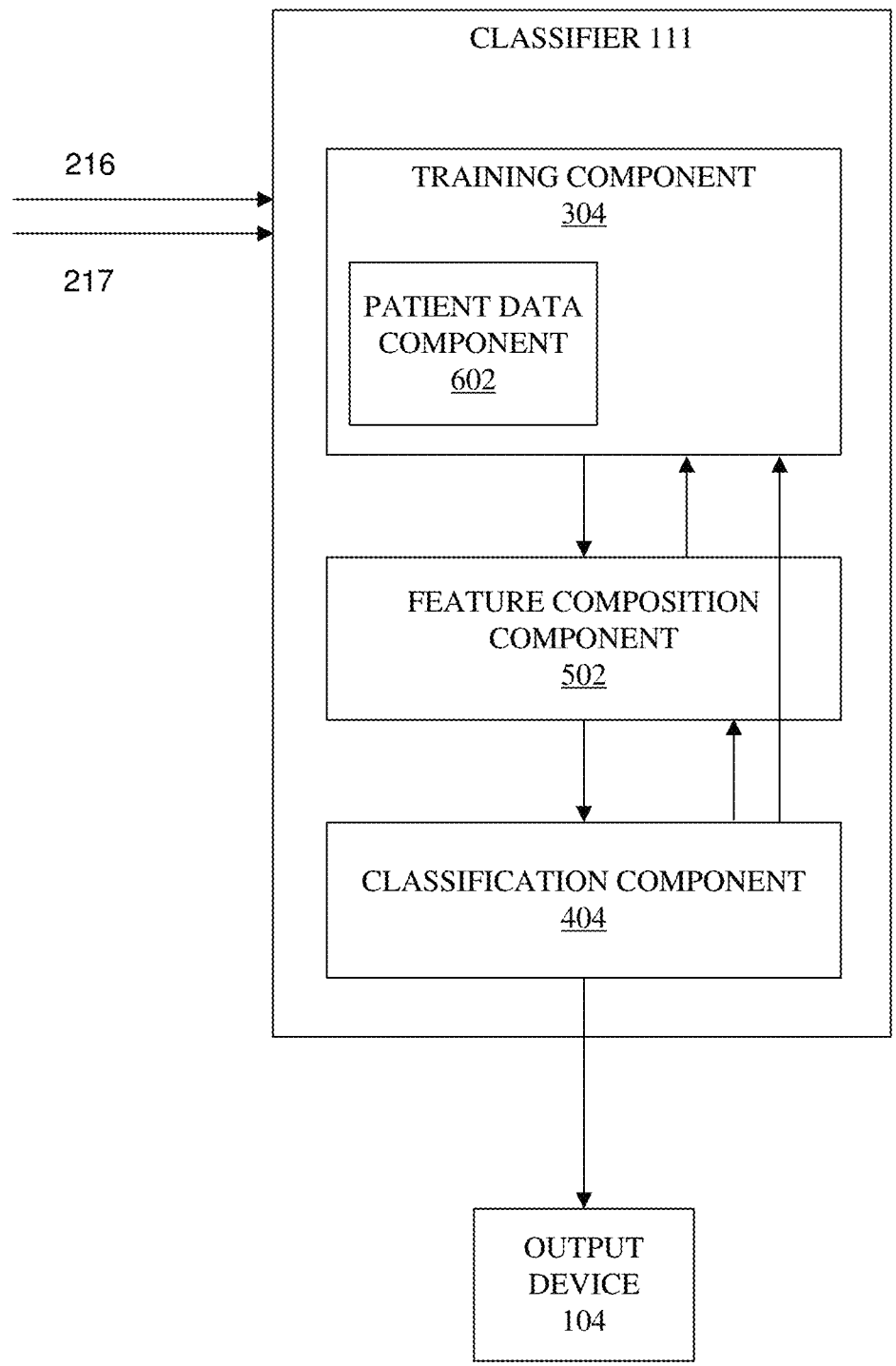
FIG. 6 illustrates another block diagram of an example, non-limiting computer-implemented system that elaborates on the classification component of the input-output flow of data as described with reference to FIG. 3.

FIG. 6 illustrates another block diagram of an example, non-limiting computer-implemented system that elaborates on the classification component of the input-output flow of data as described with reference to FIG. 3. The block diagram comprises classifier 111, and output device 104 of FIG. 1, communication channels 216, 217, and 218 of FIG. 2, training component 304 of FIG. 3, classification component 404 of FIG. 4 and feature composition component 502 of FIG. 5.

The training component 304 can further include a patient data component 602 which can store patient metadata information from the inputs block 100 of FIG. 1. The inputs that pertain to the training component can include labels of medical information and patient metadata which serve as primary resources for the classifier 111. A further aspect of the classifier can include inputs in the form of feature vectors received through communication channel 217 for re-training and can also include diagnostic results from domain experts who can provide further analysis and feedback on the outputs generated by the computer-system.

Figure 7:
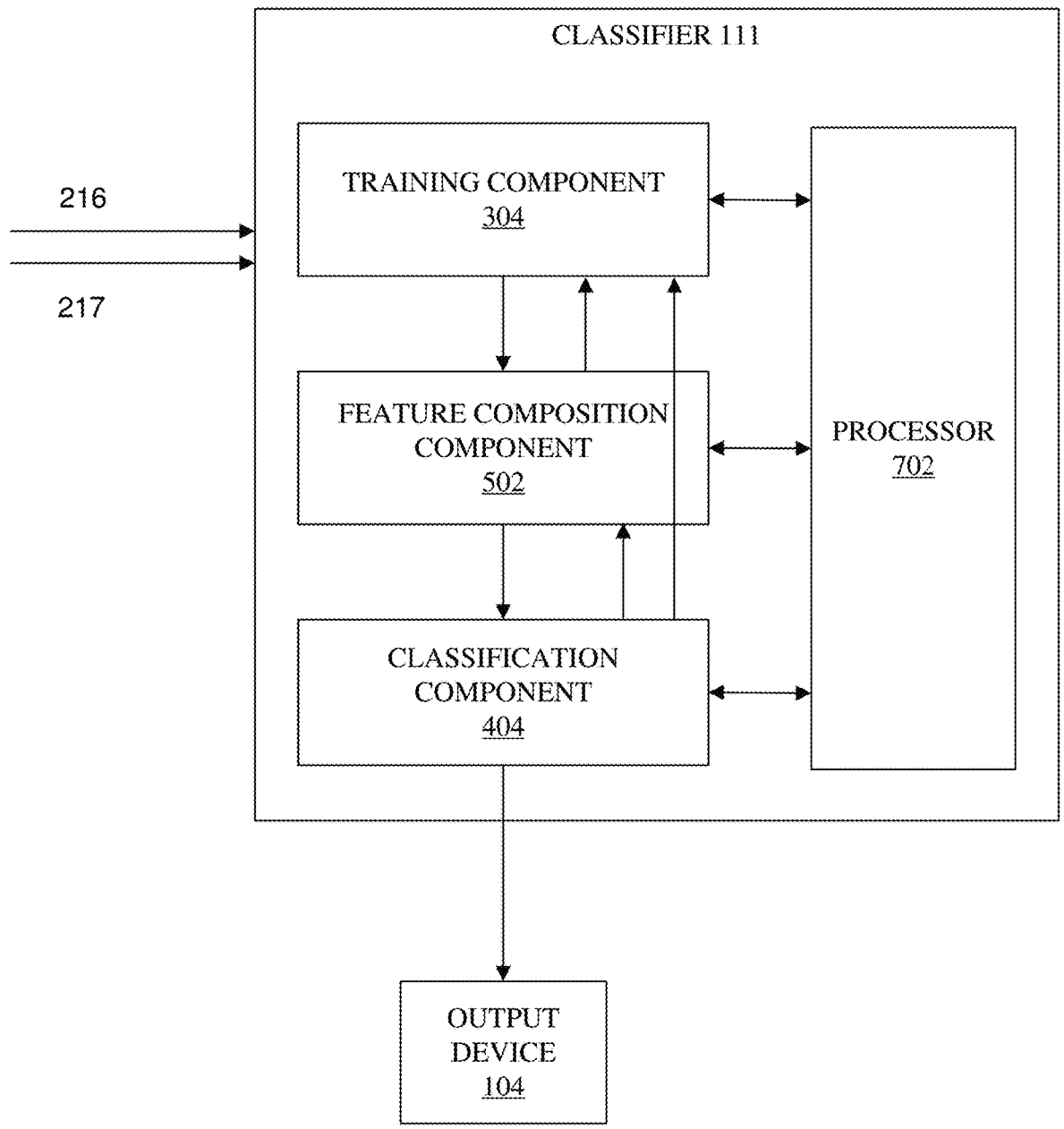
FIG. 7 illustrates another block diagram of an example, non-limiting computer-implemented system that elaborates on the classification component of the input-output flow of data as described with reference to FIG. 3.

FIG. 7 illustrates another block diagram of an example, non-limiting computer-implemented system that elaborates on the classification component of the input-output flow of data as described with reference to FIG. 3. The block diagram comprises classifier 111, and output device 104 of FIG. 1, communication channels 216, 217, and 218 of FIG. 2, training component 304 of FIG. 3, classification component 404 of FIG. 4 and feature composition component 502 of FIG. 5.

The classifier 111 can further include a processor 702 that can provide control and assistance to the training component 304, the feature composition component 502, and/or the classification component 404. The processor 702 can assist components by executing algorithms, portions of algorithms, and the like for one or more of the components of FIG. 7 to ensure that one or more of the components do not become a bottleneck in the performance of the classifier 111.

Figure 8:
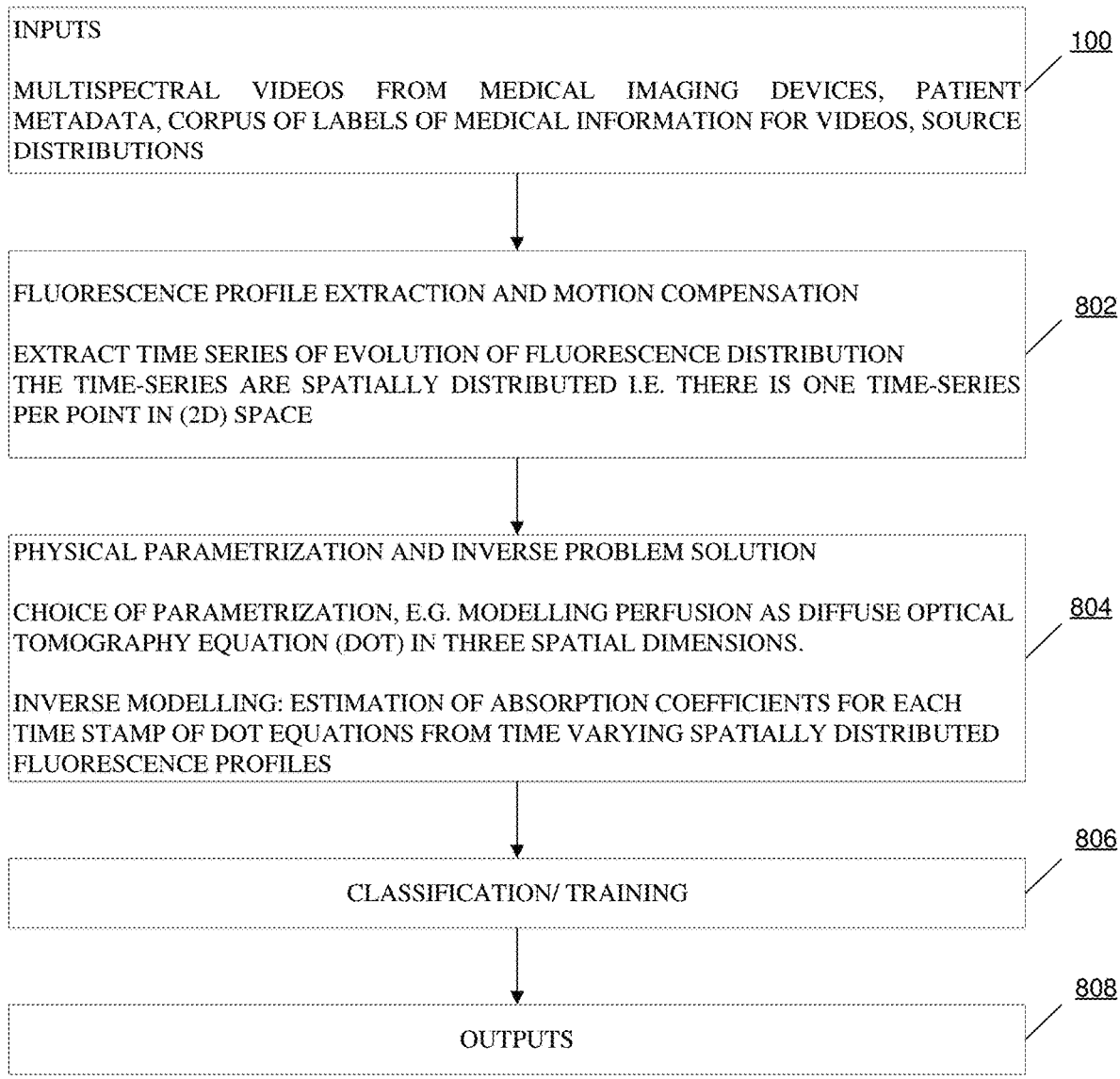
FIG. 8 illustrates a block diagram of an example, non-limiting computer-implemented method that elaborates on the input-output flow of data that facilitates diagnosis of the section of bodily tissue as described by the system discussed with reference to FIG. 1.
Figure 9:
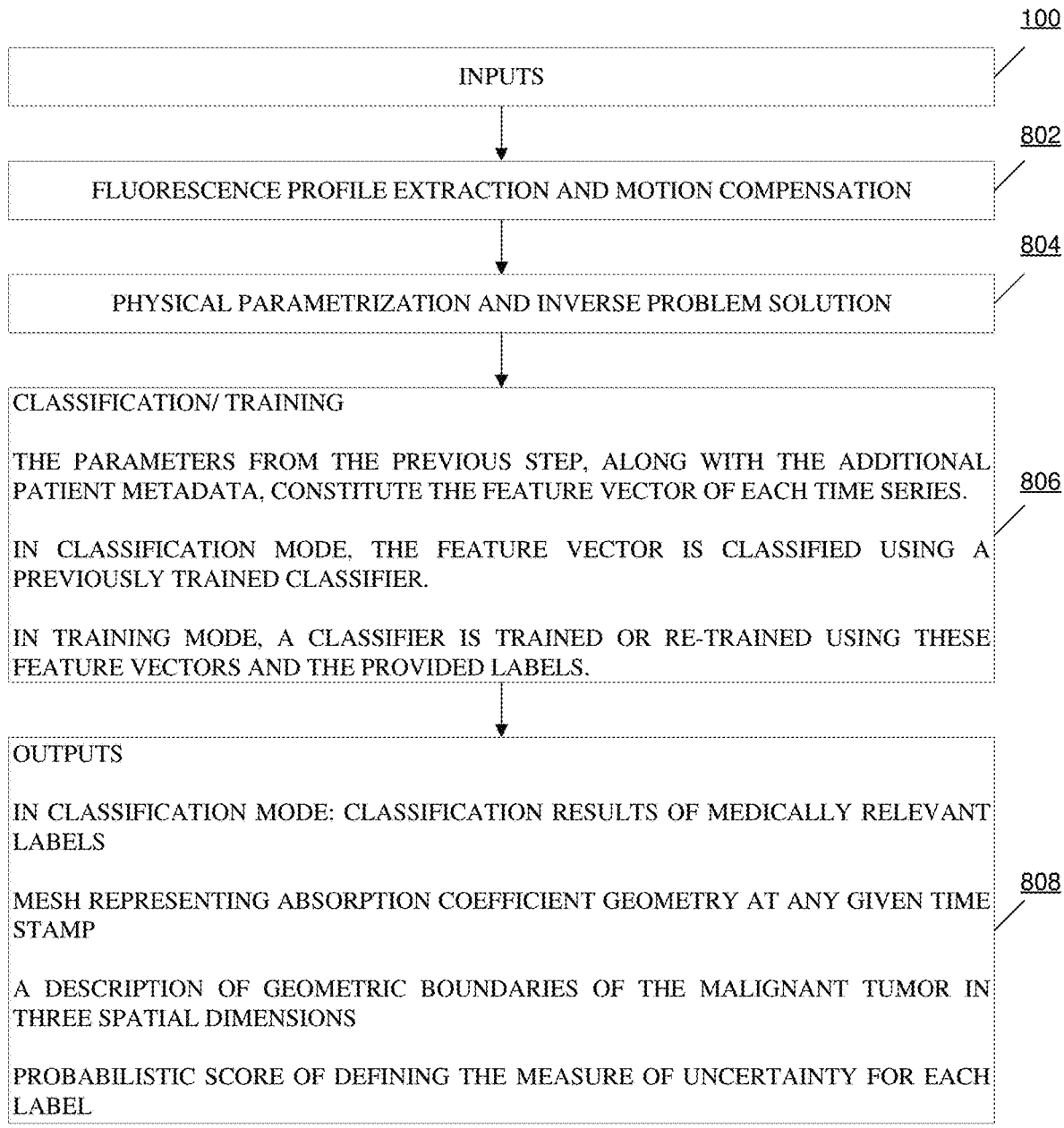
FIG. 9 illustrates a block diagram of an example, non-limiting computer-implemented method that elaborates on the input-output flow of data that facilitates diagnosis of the section of bodily tissue as described by the system discussed with reference to FIG. 1.

FIG. 8 and FIG. 9 illustrate a block diagram of an example, non-limiting computer-implemented method that elaborates on the input-output flow of data that facilitates diagnosis of the section of bodily tissue as described by the system discussed with reference to FIG. 1.

The computer-implemented system coupled with the processor addressed in one or more embodiments herein can receive input information in the form of multispectral videos, patient metadata, a corpus of labels of medical information for videos and/or source distributions which can represent feature vectors for the section of bodily tissue. Multispectral videos can be generated by one or more medical imaging devices and the corpus of labels of medical information can be used by the computer-implemented system to classify and diagnose the section of bodily tissue as a biopsy candidate or non-biopsy candidate. Patient metadata can be clinical or non-clinical and can include such information as the medical history of the patient, user profile of the patient, age, prior conditions, and other relevant patient data. Feature vectors can be extracted from one or more absorption coefficients representing time-series of fluorescence data at the section of bodily tissue. In some embodiments, it can be more efficient to extract feature vectors locally which can prevent incurring overheads arising from transmitting or streaming potentially large videos over networks inside other medical facilities such as hospitals. In other embodiments, it can become necessary to transmit the potentially large videos to other facilities to extract the feature vectors. In one embodiment, inputs can also be received in the form of physical parametrized models as generated by the computer-implemented method upon evaluation of the on-tissue dye dynamics at the section of bodily tissue. These models can be employed in the training and classification phase of the method wherein supervised machine-learning algorithms can use them to train the classification model for generating better diagnosis for the underlying tissue.

Multispectral videos from inputs block 100 can be further evaluated at the fluorescence profile extraction and motion compensation block 802 wherein time-series of fluorescence intensities representing on-tissue dye dynamics can be recorded by the computer system from multispectral videos such that there is one-time series per point in two-dimensions (2D). The physical parametrization and inverse problem solution block 804 can mathematically evaluate the time-series data such that absorption coefficients from time-series of fluorescence intensities can be estimated by the processor of the computing system using one or more algorithms for the estimation. A model representing the on-tissue dye dynamics in three dimensions based on one or more estimated absorption coefficients can be generated by the computing system. The parameters computed in the previous step can be further evaluated by the processor in conjunction with patient metadata to generate feature vectors for time-series of fluorescence at every voxel. A voxel is a data point defined on a regular grid in three-dimensions (3D) such that several voxels combine to define the physical characteristics of a volume such as tissue. In this manner, feature vectors can present information about the physical boundary of the tissue as well as about the classification of the type of tissue since the optical properties of the tissue will generate varying degrees of time varying fluorescence.

Classification/training block 806 can represent the classification aspect of the computer system wherein feature vectors classified using a classifier as represented by classifier 111 of FIG. 1 of the computer-implemented system. The classifier can attribute a diagnosis to the tumor and the outputs produced by the computer-implemented system, including the physical model, can be represented at outputs block 808.

The classifier of the computer system can assign medically relevant labels to the tissue feature vectors based on the input information it receives as part of its training phase such that the section of tissue can be diagnosed as a biopsy or a non-biopsy candidate. As discussed in one or more embodiments herein, in one aspect of the classification, the labels of medical information and feature vectors generated by components of the computing system can also act as feedback to re-train the classifier of the computing system so that more accurate assignments to tissue or sections of tissues can be made in the future.

Outputs block 808 comprises the various output information that can be generated by the computer system. The computer system outputs a mesh representing absorption geometry, a 3D model of the tissue boundaries with its underlying physical boundaries, as well as probabilistic scores for labels assigned to the feature vectors, describing the labels' accuracy. Additionally, the geometric description of the tissue in 3D can be made available to medical professionals for viewing and further diagnosis via a graphical user interface of a display of the computing system in the form of Augmented Reality (AR).

Figure 10:
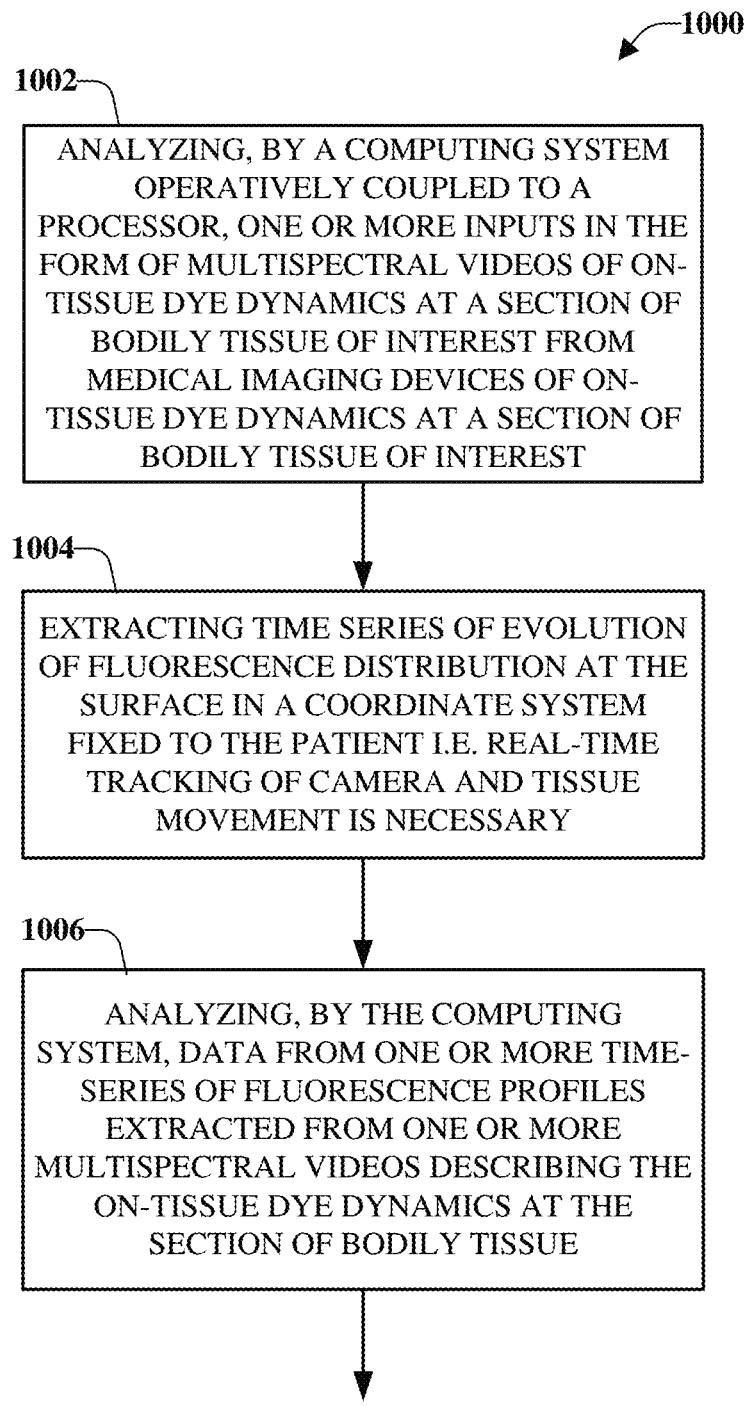
FIG. 10 illustrates a block diagram of an example, non-limiting computer-implemented system that analyzes inputs in the form of one or more multispectral videos that track time-series of fluorescence profiles in real-time representative of on-tissue dye dynamics at a section of bodily tissue of interest FIG. 1.

FIG. 10 is described with reference to blocks 1002, 1004 and 1006 and illustrates a block diagram of an example, non-limiting computer-implemented system that analyzes inputs in the form of one or more multispectral videos that track time-series of fluorescence profiles in real-time representative of on-tissue dye dynamics at a section of bodily tissue of interest FIG. 1. The system 1000 includes block 1002 wherein a computer operatively coupled to a processor analyzes input data in the form of one or more multispectral videos. Repetitive description of like elements employed in other embodiments described herein is omitted for sake of brevity. Multispectral videos representing on-tissue dye dynamics can be produced from one or more medical imaging devices. When a fluorescent dye is administered to a patient at the section of bodily tissue, the rate of fluorescence emission by sections of the tissue can be recorded as primary data, which can be further processed to record one or more time-series of evolution of fluorescence. The time-series data can be recorded at the surface of the section of bodily tissue based on real-time tracking of camera and tissue movement. The computer system further analyzes the one or more time-series of fluorescence distributions and produces a new set of information which can be used to generate absorption coefficients geometry representing the tumor boundary.

Figure 11:
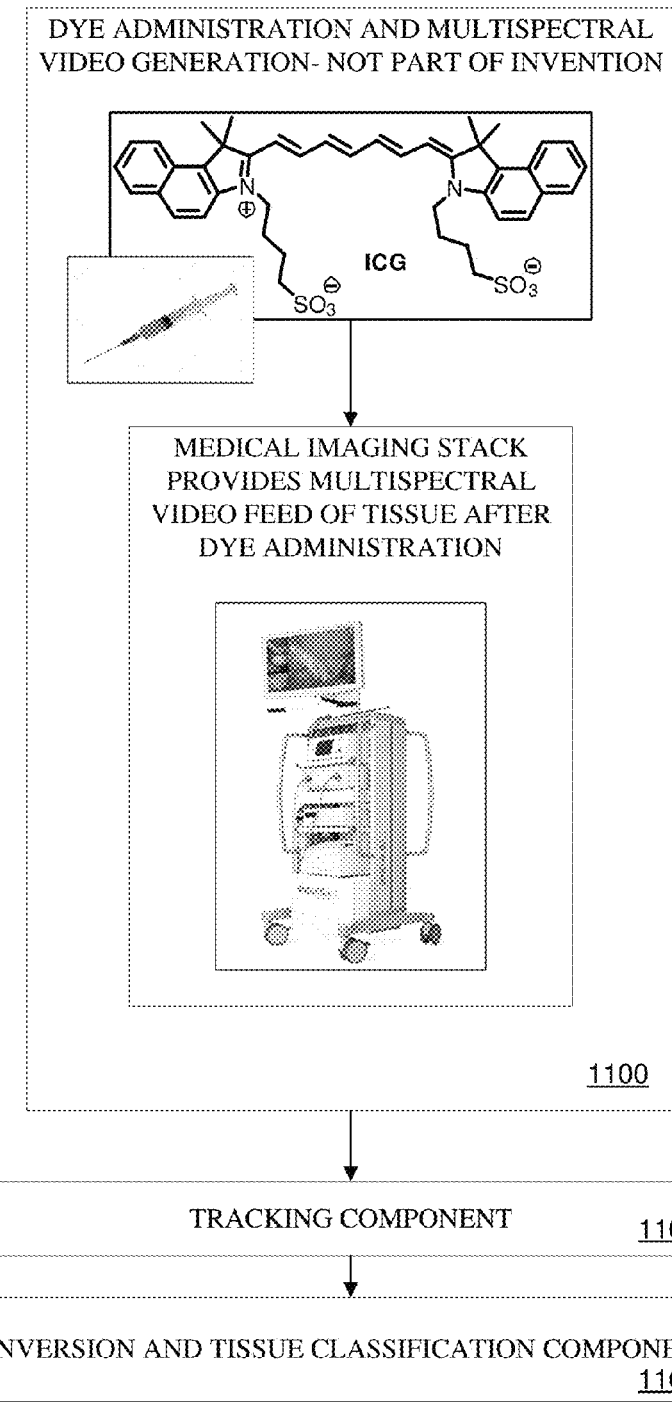
FIG. 11 illustrates a block diagram of an example, non-limiting embodiment describing tumor boundary delineation in colorectal surgery in accordance with one or more embodiments described herein.

FIG. 11 illustrates a block diagram of an example, non-limiting embodiment describing tumor boundary delineation in colorectal surgery in accordance with one or more embodiments described herein. After administering the dye Indocyanine Greene (ICG) at the section of tissue of interest, the medical imaging device monitors the fluorescence and generates multispectral video feed at block 1100. The multispectral videos can be sent to tracking component 1102 for extracting a secondary set of data wherein the extraction is based on absorption coefficients of fluorescence time-series. This secondary data can be fed to inversion and tissue classification component 1104.

Figure 12:
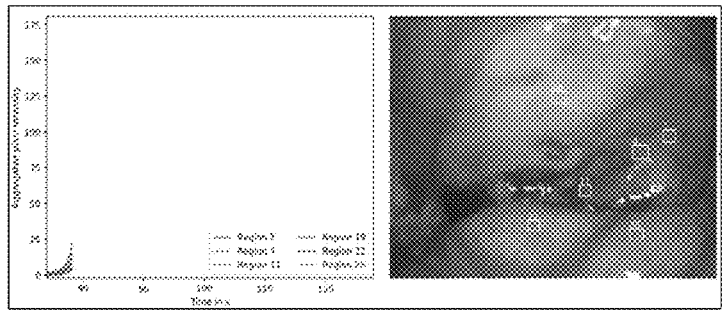
FIG. 12 illustrates another block diagram of an example, non-limiting embodiment describing tumor boundary delineation in colorectal surgery in accordance with one or more embodiments described herein.
Figure 12:
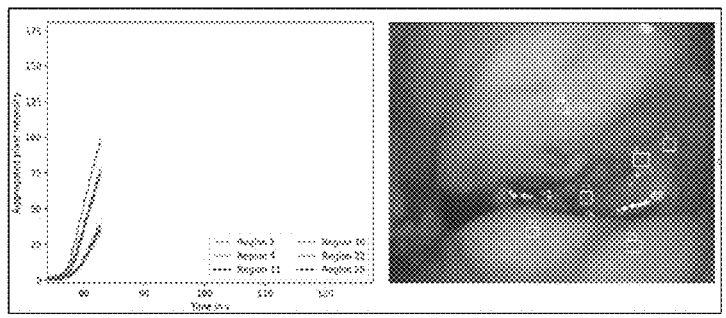
Figure 12:
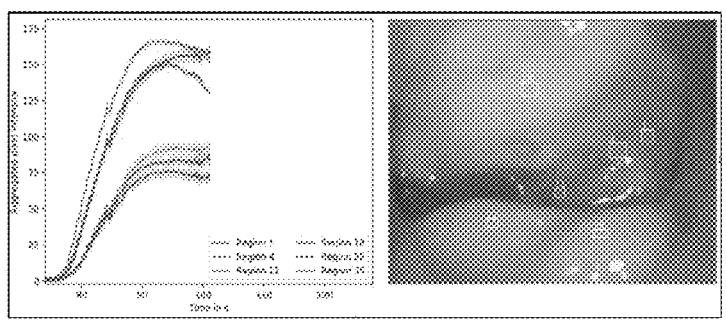

FIG. 12 illustrates a block diagram of an example, non-limiting embodiment describing tumor boundary delineation in colorectal surgery in accordance with one or more embodiments described herein. The components of the block diagram include dye administration and multispectral video generation 1100 and inversion and tissue classification component 1104 of FIG. 11. Herein the tracking component 1202 describes different phases of the time-varying fluorescence observed within the colorectal region of interest. The white squares in each of the three phases represent the points on the tissue where fluorescence is monitored, and a graph of aggregated pixel intensity versus time in seconds (s) is generated as live data. Each of the colors in the graph represent a single point or region around the point being monitored. Evidently, the tissue region being monitored turns completely fluorescent with the emission of light over time and specific regions of the tissue can be zoomed onto over the progression. The recorded graph is the time-series of fluorescence.

Figure 13:
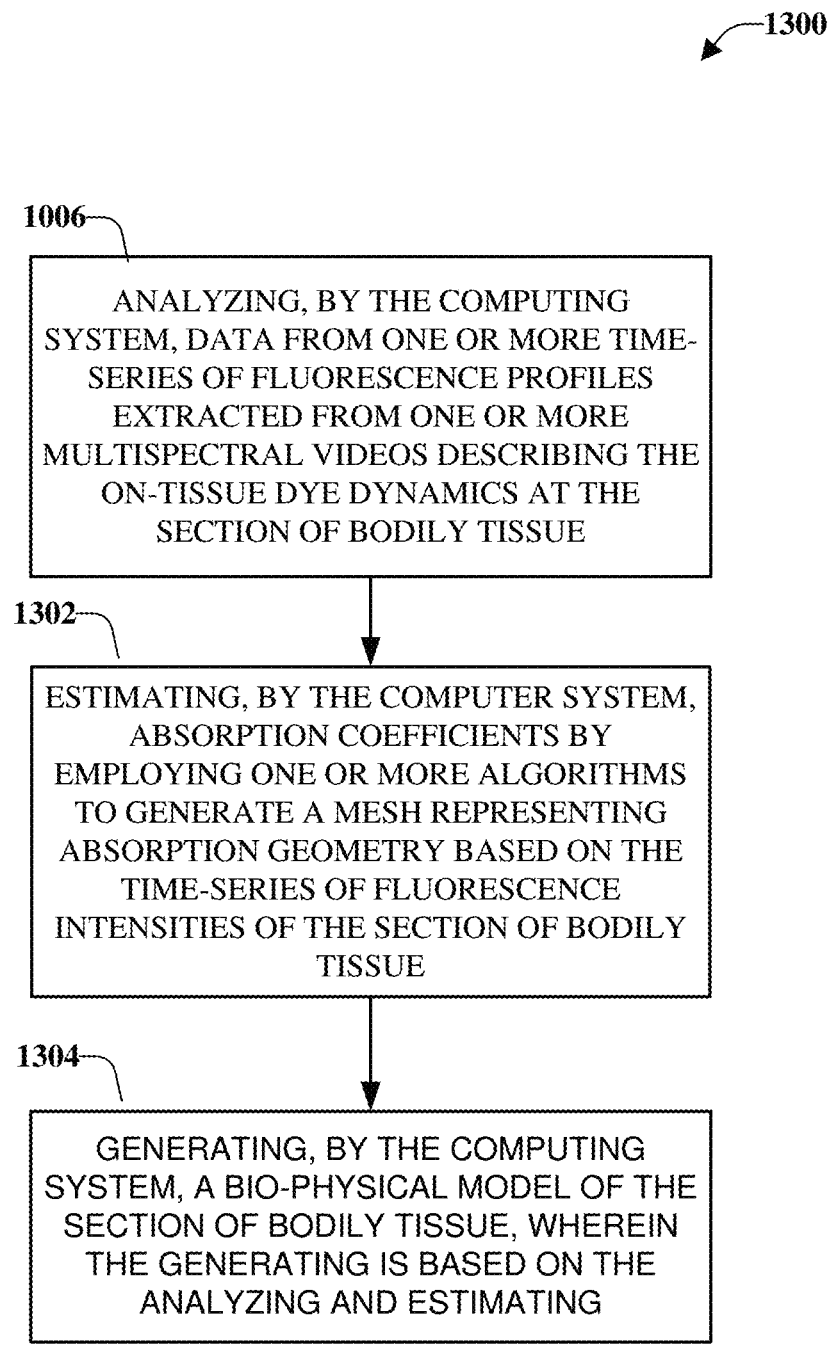
FIG. 13 illustrates a block diagram of an example, non-limiting computer-implemented system that analyzes data from one or more time-series of fluorescence profiles extracted from one or more multispectral videos describing the on-tissue dye dynamics at the section of bodily tissue to generate a bio-physical model of the section of bodily tissue.

FIG. 13 is described with reference to blocks 1006, 1302 and 1304 and illustrates a block diagram of an example, non-limiting computer-implemented system that analyzes data from one or more time-series of fluorescence profiles extracted from one or more multispectral videos describing the on-tissue dye dynamics at the section of bodily tissue to generate a bio-physical model of the section of bodily tissue. The system 1300 includes block 1006 of FIG. 10 wherein the computer operatively coupled to a processor can generate and analyze time-series data representing the dye-dynamics at the section of bodily tissue to further extract absorption coefficients for the section of tissue and blocks 1302 and 1304. The computer system can use the time-series data to estimate absorption coefficient geometry by modelling the on-tissue dye dynamics as an inverse problem for DOT equations in 3D. The absorption coefficients are estimated from time-series of fluorescence data by the processor of the computing system using algorithms for the estimation and feature vectors are extracted from the absorption coefficient data, as discussed in one or more embodiments herein. Repetitive description of like elements employed in other embodiments described herein is omitted for sake of brevity. As a result, a mesh representing absorption coefficient geometry in 3D can be generated by the computer and together with the feature vector information, the computing system generates a bio-physical model representing the visible and invisible boundaries of the tumor. The bio-physical model can be assigned one or more labels and a confidence score to the labels by correlation wherein correlation comprises agreement with the internal representation of the feature space learned by the classifier of the computing system such that it can assign one or more labels to one or more feature vectors by choosing labels from memory whose features can be a best match for the unseen example.

Figure 14:
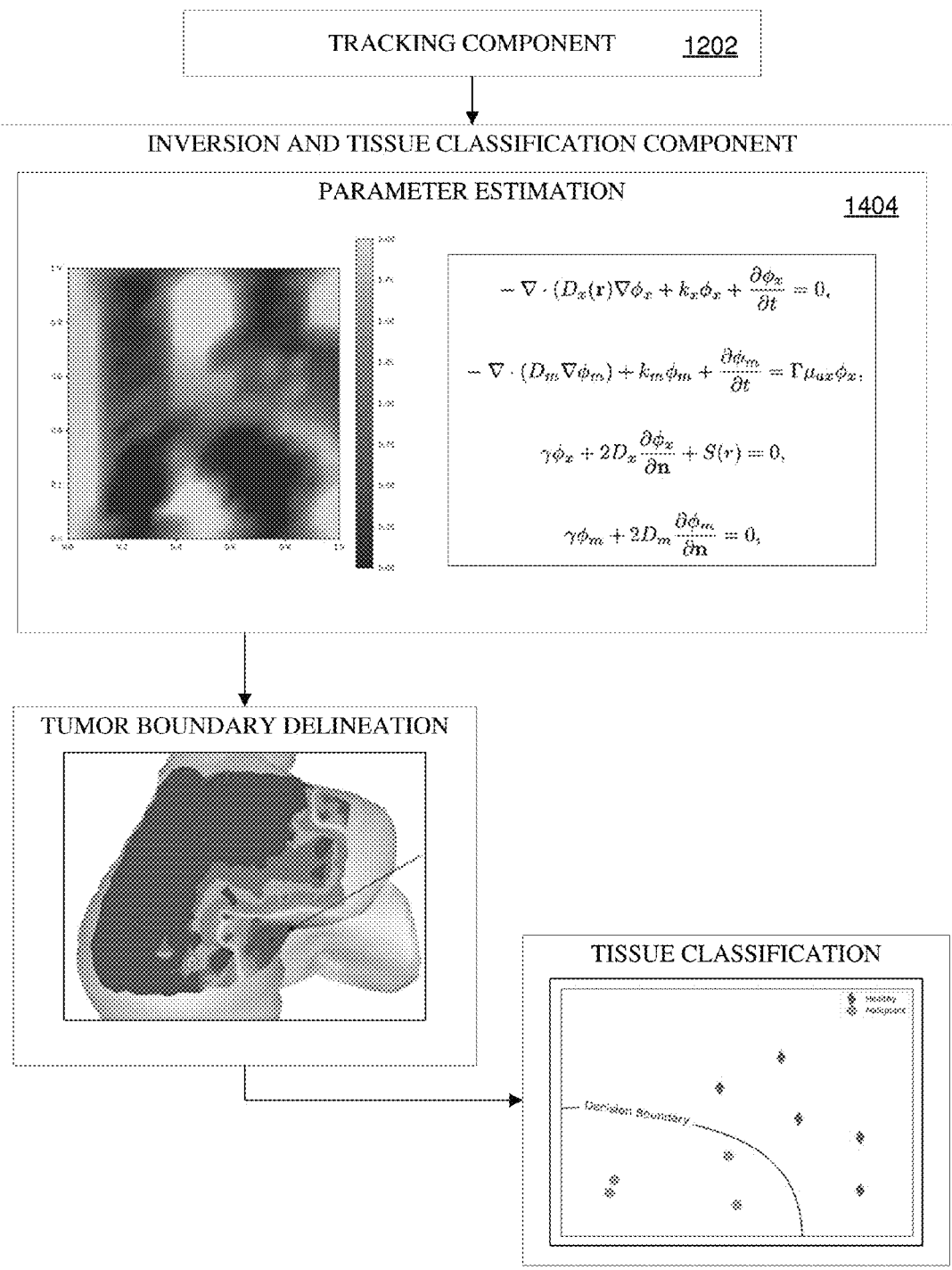
FIG. 14 illustrates another block diagram of an example, non-limiting embodiment describing tumor boundary delineation in colorectal surgery in accordance with one or more embodiments described herein.

FIG. 14 illustrates another block diagram of an example, non-limiting embodiment describing tumor boundary delineation in colorectal surgery in accordance with one or more embodiments described herein. Tracking component 1202 provides the secondary set of extracted data to inversion and tissue classification component 1402. At the parameter estimation phase, machine learning algorithms based on partial differential equations are used to extract absorption coefficient parameters from the set of time-series data received. In an example, the computer system can output a mesh representing a time-varying, 3D absorption coefficient geometry. Upon further analysis of the absorption coefficient, a 3D model describing the underlying tumor boundaries can be output by the computer system and can further classified. The tissue classification image describes how data points for sections of the tumor that fall to the bottom left of the decision boundary are classified as malignant, while those that fall outside of the boundary are considered benign.

Figure 15:
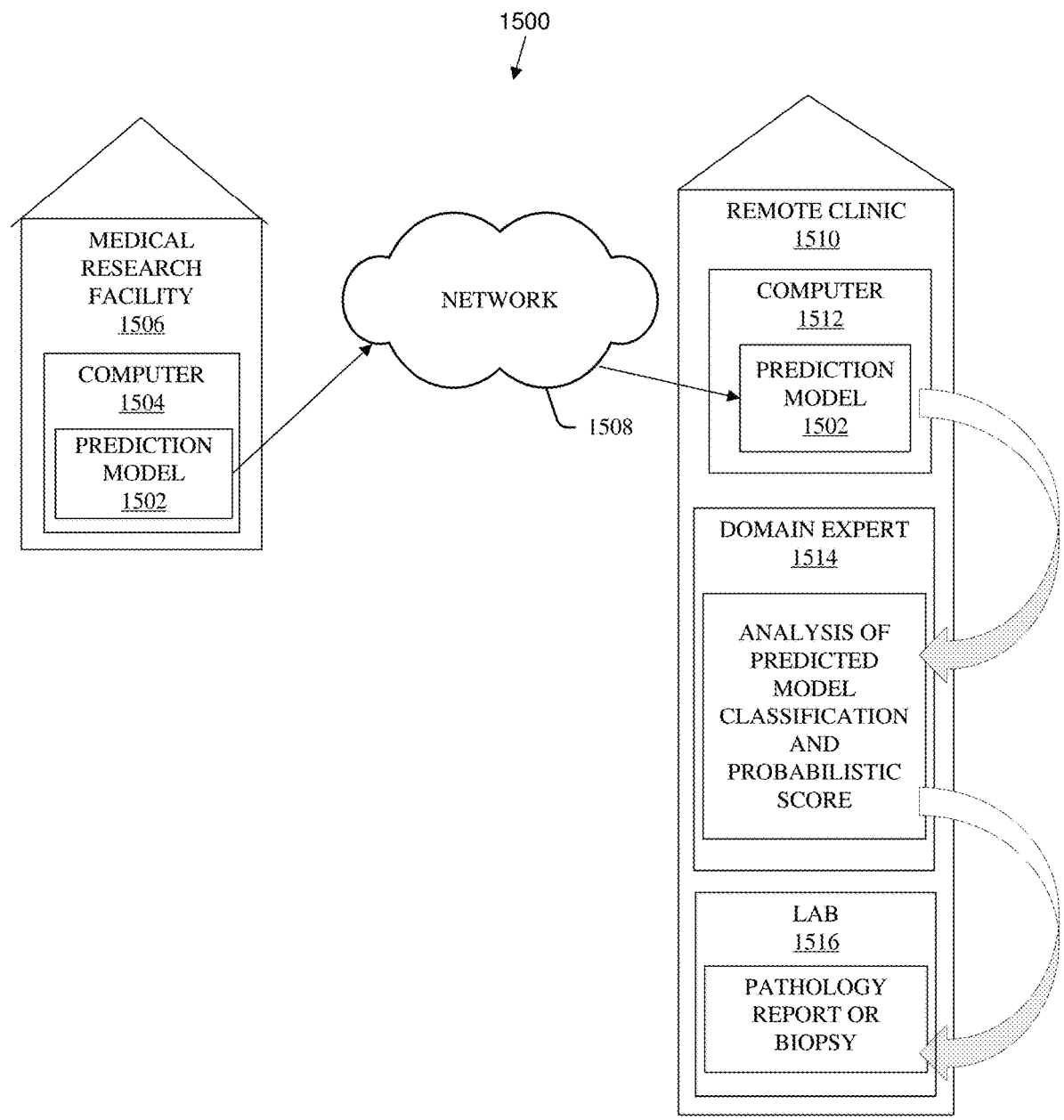
FIG. 15 illustrates a block diagram of an example, non-limiting block diagram of a system and environment for creating a prediction model that facilitates better diagnoses of medical conditions in accordance with one or more embodiments described herein.

FIG. 15 illustrates a block diagram of an example, non-limiting block diagram of a system and environment for creating a prediction model that facilitates better diagnoses of medical conditions in accordance with one or more embodiments described herein. Repetitive description of like elements employed in other embodiments described herein is omitted for sake of brevity. The prediction model 1502 can be generated with a computer 1504 at a medical research facility or other research and clinical facilities such as hospitals. The computer 1504 can transmit the prediction model 1502 over a network 1508 wired and/or wireless to a remote clinic 1510. The prediction model 1502 can be received by a device or computer 1512 at the remote clinic 1510 and used later to diagnose clinical patients. For example, the prediction model 1502 may be loaded into the computer 1512 at the remote clinic 1510 so that it may be sent to domain expert 1514 to be used with local diagnostic software.

The domain expert can provide further diagnosis on the classification and probabilistic score generated for the prediction model. When seeing a clinical patient, the medical expert can input a new patient's medical symptoms into the diagnostic software (SW) and this SW can then process the patient's symptoms, electronic health record, and/or image data together with the SW utilizing the prediction model 1502 to produce one or more possible causes/diagnoses of the patient's medical condition. If it is determined that a biopsy or pathological report is required, the information can be passed to a lab 1516 for the same.

Figure 16:
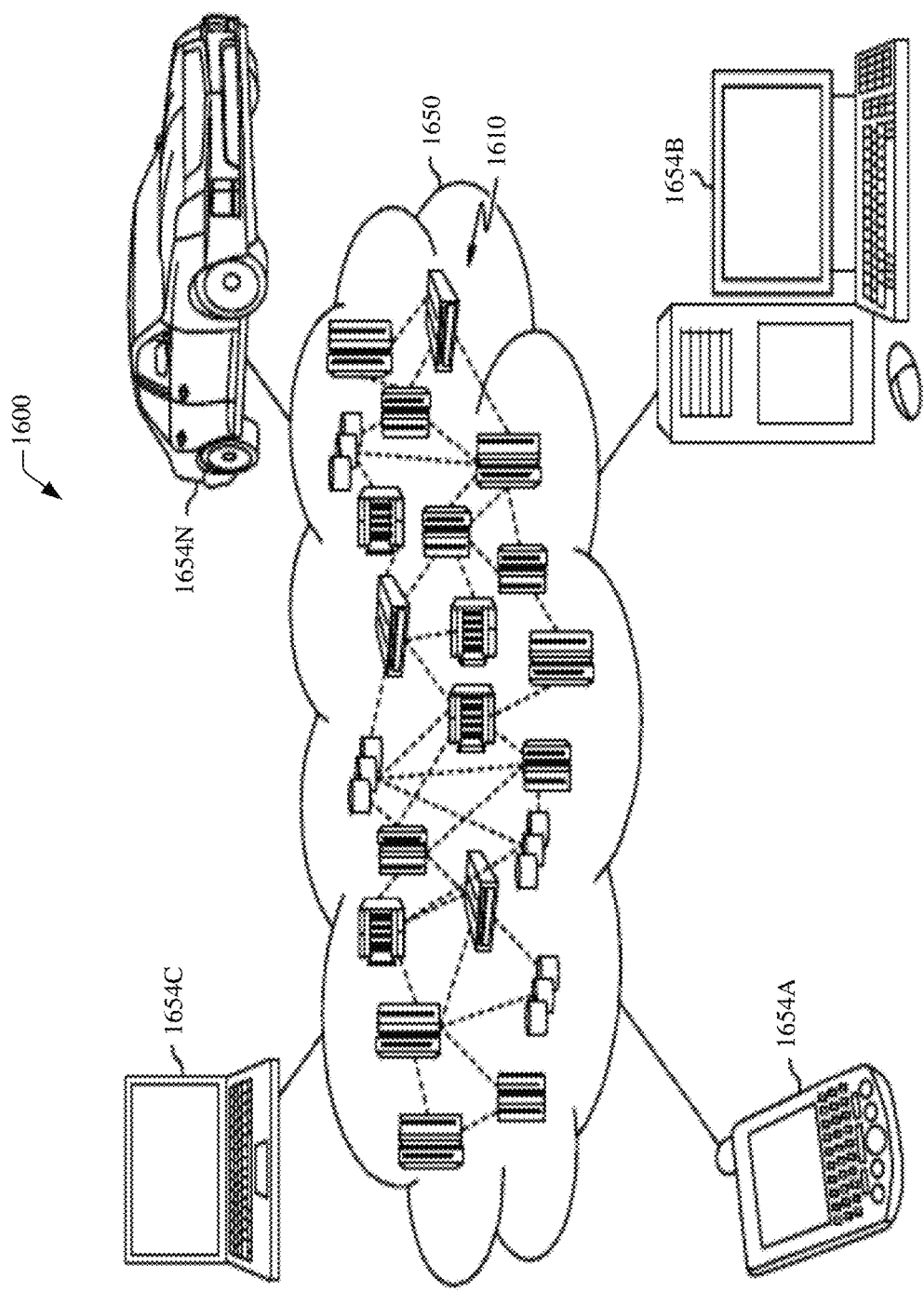
FIG. 16 is a block diagram of a non-limiting example of a cloud computing environment in accordance with one or more embodiments described herein.

FIG. 16 is a block diagram of a non-limiting example of a cloud computing environment in accordance with one or more embodiments described herein. As shown, cloud computing environment 1650 includes one or more cloud computing nodes 1610 with which local computing devices used by cloud consumers, such as, for example, personal digital assistant (PDA) or cellular telephone 1654A, desktop computer 1654B, laptop computer 1654C, and/or automobile computer system 1654N may communicate. Although not illustrated in FIG. 16, cloud computing nodes 1610 can further comprise a quantum platform (e.g., quantum computer, quantum hardware, quantum software, and/or another quantum platform) with which local computing devices used by cloud consumers can communicate. Nodes 1610 may communicate with one another. They may be grouped (not shown) physically or virtually, in one or more networks, such as Private, Community, Public, or Hybrid clouds as described hereinabove, or a combination thereof. This allows cloud computing environment 1650 to offer infrastructure, platforms and/or software as services for which a cloud consumer does not need to maintain resources on a local computing device. It is understood that the types of computing devices 1654A-N shown in FIG. 16 are intended to be illustrative only and that computing nodes 1610 and cloud computing environment 1650 can communicate with any type of computerized device over any type of network and/or network addressable connection (e.g., using a web browser).

Figure 17:
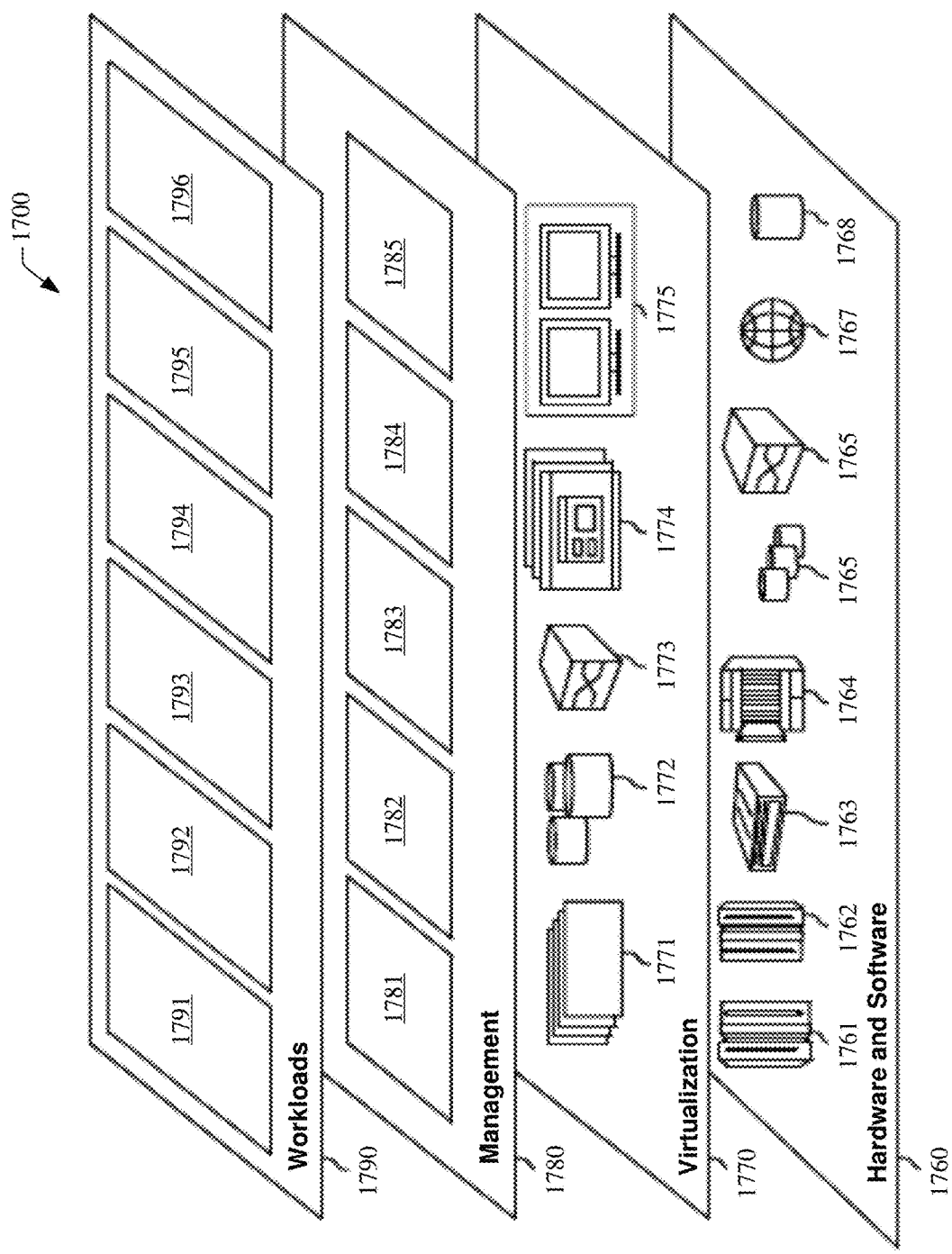
FIG. 17 is a block diagram of a non-limiting example of abstraction model layers in accordance with one or more embodiments described herein.

FIG. 17 is a block diagram of a non-limiting example of abstraction model layers in accordance with one or more embodiments described herein. It should be understood in advance that the components, layers, and functions shown in FIG. 12 are intended to be illustrative only and embodiments of the invention are not limited thereto. As depicted, the following layers and corresponding functions are provided:

Hardware and software layer 1760 include hardware and software components. Examples of hardware components include mainframes 1761; RISC (Reduced Instruction Set Computer) architecture-based servers 1762; servers 1763; blade servers 1764; storage devices 1765; and networks and networking components 1766. In some embodiments, software components include network application server software 1767, database software 1768, quantum platform routing software (not illustrated in FIG. 17), and/or quantum software (not illustrated in FIG. 17).

Virtualization layer 1770 provides an abstraction layer from which the following examples of virtual entities may be provided: virtual servers 1771; virtual storage 1772; virtual networks 1773, including virtual private networks; virtual applications and operating systems 1774; and virtual clients 1775.

In one example, management layer 1780 may provide the functions described below. Resource provisioning 1781 provides dynamic procurement of computing resources and other resources that are utilized to perform tasks within the cloud computing environment. Metering and pricing 1782 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 1783 provides access to the cloud computing environment for consumers and system administrators. Service level management 1784 provides cloud computing resource allocation and management such that required service levels are met. Service Level Agreement (SLA) planning and fulfillment 1785 provide pre-arrangement for, and procurement of, cloud computing resources for which a future requirement is anticipated in accordance with an SLA.

Workloads layer 1790 provides examples of functionality for which the cloud computing environment may be utilized.

Non-limiting examples of workloads and functions which may be provided from this layer include mapping and navigation 1791; software development and lifecycle management 1792; virtual classroom education delivery 1793; data analytics processing 1794; transaction processing 1795; and vulnerability risk assessment software 1796.

Embodiments of the present invention can be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various aspects of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to customize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 18:
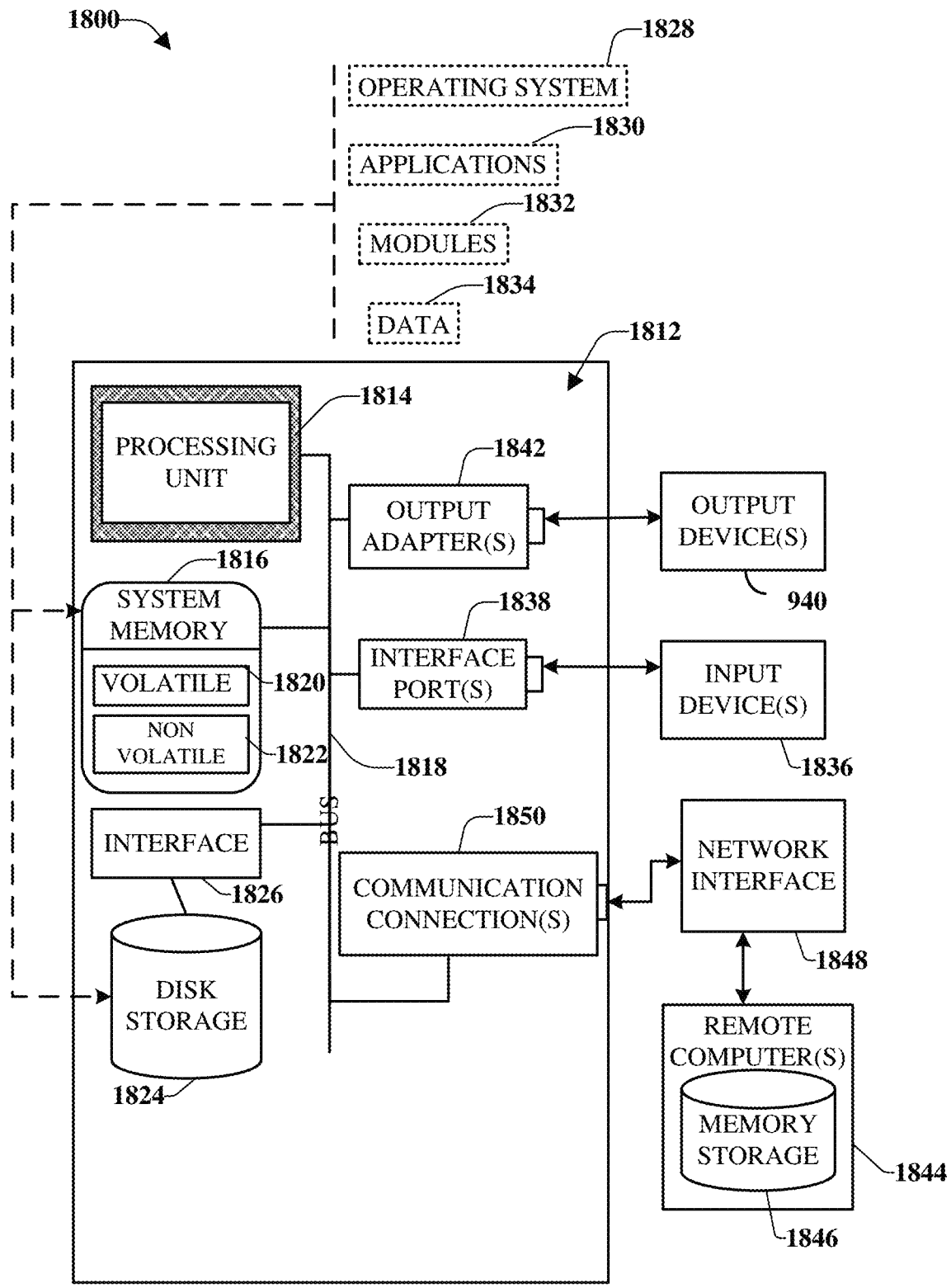
FIG. 18 illustrates a block diagram of an example, non-limiting operating environment in which one or more embodiments described herein can be facilitated.

To provide a context for the various aspects of the disclosed subject matter as well as FIG. 18, the following discussion are intended to provide a general description of a suitable environment in which the various aspects of the disclosed subject matter can be implemented. FIG. 18 illustrates a block diagram of an example; non-limiting operating environment in which one or more embodiments described herein can be facilitated. Repetitive description of like elements employed in other embodiments described herein is omitted for sake of brevity. With reference to FIG. 18, a suitable operating environment 1800 for implementing various aspects of this disclosure can also include a computer 1812. The computer 1812 can also include a processing unit 1814, a system memory 1816, and a system bus 1818. The system bus 1818 couples system components including, but not limited to, the system memory 1816 to the processing unit 1814. The processing unit 1814 can be any of various available processors. Dual microprocessors and other multiprocessor architectures also can be employed as the processing unit 1814. The system bus 1818 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1394), and Small Computer Systems Interface (SCSI).

The system memory 1816 can also include volatile memory 1820 and nonvolatile memory 1822. The basic input/output system (BIOS), containing the basic routines to transfer information between elements within the computer 1812, such as during start-up, is stored in nonvolatile memory 1822. By way of illustration, and not limitation, nonvolatile memory 1822 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 820 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1812 can also include removable/non-removable, volatile/non-volatile computer storage media. FIG. 18 illustrates, for example, a disk storage 1824. Disk storage 1824 can also include, but is not limited to, devices like a magnetic disk drive, floppy disk drive, tape drive, Jaz drive, Zip drive, LS-100 drive, flash memory card, or memory stick. The disk storage 1824 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1824 to the system bus 1818, a removable or non-removable interface is typically used, such as interface 1826. FIG. 18 also depicts software that acts as an intermediary between users and the basic computer resources described in the suitable operating environment 1800. Such software can also include, for example, an operating system 1828. Operating system 1828, which can be stored on disk storage 1824, acts to control and allocate resources of the computer 1812.

System applications 1830 take advantage of the management of resources by operating system 828 through program modules 1832 and program data 1834, e.g., stored either in system memory 1816 or on disk storage 1824. It is to be appreciated that this disclosure can be implemented with various operating systems or combinations of operating systems. A user enters commands or information into the computer 1812 through input device(s) 1836. Input devices 1836 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1814 through the system bus 1818 via interface port(s) 1838. Interface port(s) 1838 include, for example, a serial port, a parallel port, a game port, and a universal serial bus (USB). Output device(s) 1840 use some of the same type of ports as input device(s) 1836. Thus, for example, a USB port can be used to provide input to computer 1812, and to output information from computer 1812 to an output device 1840. Output adapter 1842 is provided to illustrate that there are some output devices 1840 like monitors, speakers, and printers, among other output devices 1840, which require special adapters. The output adapters 1842 include, by way of illustration and not limitation, video and sound cards that provide a means of connection between the output device 1840 and the system bus 1818. It should be noted that other devices and/or systems of devices provide both input and output capabilities such as remote computer(s) 1844.

Computer 1812 can operate in a networked environment using logical connections to one or more remote computers, such as remote computer(s) 1844. The remote computer(s) 1844 can be a computer, a server, a router, a network PC, a workstation, a microprocessor based appliance, a peer device or other common network node and the like, and typically can also include many or all of the elements described relative to computer 1812. For purposes of brevity, only a memory storage device 1846 is illustrated with remote computer(s) 1844. Remote computer(s) 1844 is logically connected to computer 1812 through a network interface 1848 and then physically connected via communication connection 1850. Network interface 1848 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 1850 refers to the hardware/software employed to connect the network interface 1848 to the system bus 1818. While communication connection 1850 is shown for illustrative clarity inside computer 1812, it can also be external to computer 1812. The hardware/software for connection to the network interface 1848 can also include, for exemplary purposes only, internal and external technologies such as, modems including regular telephone grade modems, cable modems and DSL modems, ISDN adapters, and Ethernet cards.

Figure 19:
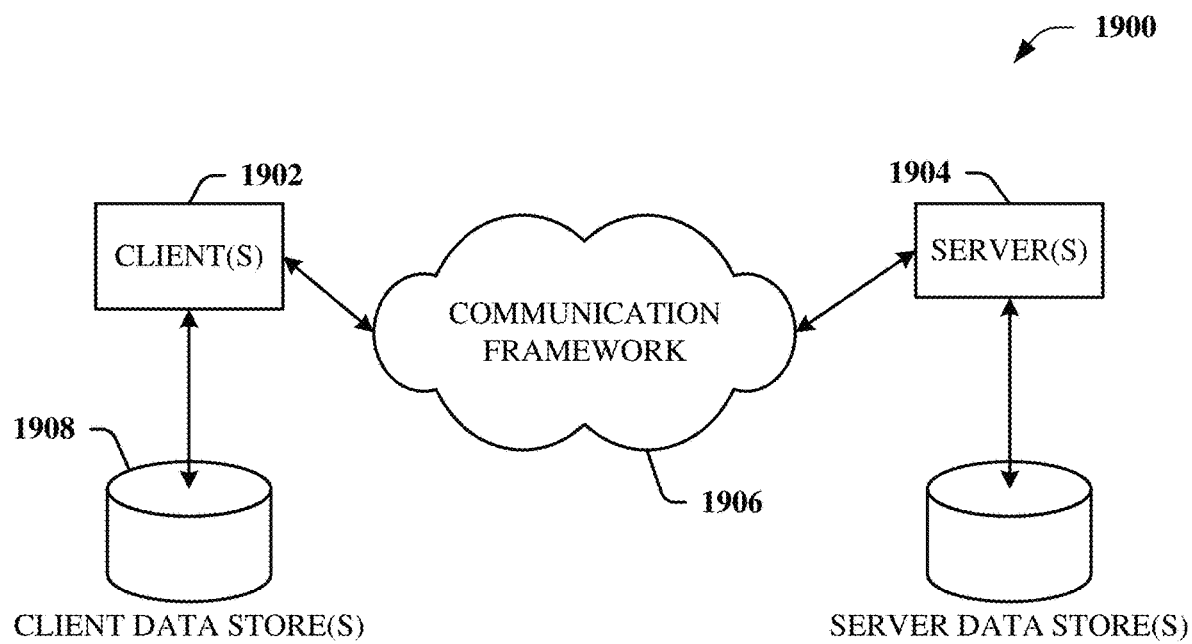
FIG. 19 illustrates an example, non-limiting, networking environment in which one or more embodiments described herein can be facilitated.

FIG. 19 illustrates an example, non-limiting; networking environment in which one or more embodiments described herein can be facilitated. The sample computing environment 1900 includes one or more client(s) 1902. The client(s) 1902 can be hardware and/or software (e.g., threads, processes, computing devices). The sample computing environment 1900 also includes one or more server(s) 1904. The server(s) 1904 can also be hardware and/or software (e.g., threads, processes, computing devices). The servers 1904 can house threads to perform transformations by employing one or more embodiments as described herein, for example. One possible communication between a client 1902 and servers 1904 can be in the form of a data packet adapted to be transmitted between two or more computer processes. The sample computing environment 1900 includes a communication framework 1906 that can be employed to facilitate communications between the client(s) 1902 and the server(s) 1904. The client(s) 1902 are operably connected to one or more client data store(s) 1908 that can be employed to store information local to the client(s) 1902. Similarly, the server(s) 1904 are operably connected to one or more server data store(s) 1910 that can be employed to store information local to the servers 1904.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc.

that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed:

1. A system, comprising:
a memory; and
a processor that executes computer-executable components stored in the memory, the computer-executable components comprising:
a feature composition component that extracts one or more feature vectors from a time-series evolution of fluorescence distribution observed at a section of bodily tissue of interest, wherein the one or more feature vectors represent a physical model describing on-tissue dye dynamics of the section of bodily tissue; and
a classification component of a classifier, wherein the classification component generates a classification attribute for the section of bodily tissue represented by the one or more feature vectors which allows the classifier to designate the section of bodily tissue as a biopsy or a non-biopsy candidate through execution of one or more supervised machine learning algorithms.

2. The system of claim 1, wherein the computer-executable components further comprise:
a time-series generation component that generates one or more spatially distributed time-series of fluorescence intensities, from multispectral video streams generated by one or more medical imaging devices, as a result of on-tissue dye dynamics at the section of bodily tissue.

3. The system of claim 2, wherein the computer-executable components further comprise:
an absorption coefficient estimation component that estimates one or more absorption coefficients from the one or more spatially distributed time-series of fluorescence intensities as an inverse problem for one or more Diffuse Optical Tomography (DOT) equations.

4. The system of claim 3, wherein the absorption coefficient estimation component employs the one or more Diffuse Optical Tomography (DOT) equations as a choice of parametrization to generate the on-tissue dye dynamics in three-dimensions.

5. The system of claim 4, wherein the computer-executable components further comprise:
a feature vector extraction component wherein the absorption coefficient estimation component analyzes one or more parameters in conjunction with additional inputs of patient metadata to generate the one or more feature vectors for time-series of fluorescence distribution at one or more voxels in three-dimensions, wherein one voxel of the one or more voxels is a data point defined on a regular grid in three-dimensions (3D) such that several voxels combine to define physical characteristics of a volume such as tissue.

6. The system of claim 1, wherein the classification component of the classifier also assigns labels indicative of medical information to the one or more feature vectors through the one or more supervised machine learning algorithms, by using inputs in a form of clinical data, non-clinical data or patient metadata.

7. The system of claim 6, wherein the classification component of the classifier further assigns a probabilistic score to indicate a measure of uncertainty of one or more of the labels indicative of medical information, wherein the one or more of the labels are applied using the one or more supervised machine learning algorithms.

8. A computer-implemented method, comprising:
extracting, by a computing system operatively coupled to a processor, one or more feature vectors from a time-series evolution of fluorescence distribution observed at a section of bodily tissue of interest, wherein the one or more feature vectors represent a physical model describing on-tissue dye dynamics of the section of bodily tissue;
generating, by the computing system, a classification attribute for the section of bodily tissue represented by the one or more feature vectors, wherein a classifier designates the section of bodily tissue as a biopsy or a non-biopsy candidate through execution of one or more supervised machine learning algorithms; and
training, by the computing system, a classification component of the computing system through supervised machine learning to classify a particular group of one or more feature vectors of the section of bodily tissue of interest as biopsy candidates or non-biopsy candidates.

9. The computer-implemented method of claim 8, further comprising:
generating, by the computing system, one or more spatially distributed time-series of fluorescence intensities, from multispectral video streams representative of the on-tissue dye dynamics observed at the section of bodily tissue; and
recording, by the computing system, the time-series evolution of fluorescence distribution observed at the section of bodily tissue of interest, as a result of the on-tissue dye dynamics.

10. The computer-implemented method of claim 9, further comprising:
estimating, by the computing system, one or more absorption coefficients from the one or more spatially distributed time-series of fluorescence intensities, wherein the one or more absorption coefficients are one or more parameters for reconstruction of unseen physical characteristics of the section of bodily tissue.

11. The computer-implemented method of claim 8, further comprising generating, by the computing system, a model representing the on-tissue dye dynamics in three dimensions based on one or more estimated absorption coefficients.

12. The computer-implemented method of claim 10, further comprising:
generating, by the computing system, the one or more feature vectors based on the one or more parameters and patient metadata, wherein the generating comprises generating the one or more feature vectors for the time-series evolution of fluorescence distribution.

13. The computer-implemented method of claim 8, wherein the classification component is trained and re-trained using information from the one or more feature vectors and a corpus of labels via the one or more supervised machine learning algorithms to improve classification accuracy.

14. The computer-implemented method of claim 8, wherein the classification component is trained and re-trained via information feedback between the classification component and a training logic component of a pre-trained classifier of the computing system, and wherein the classification component is trained and re-trained based on information provided via a device associated with one or more experts in a medical community.

15. The computer-implemented method of claim 8, wherein the computing system outputs a description of geometric boundaries of the section of bodily tissue via a graphical user interface of a display of the computing system in a form of augmented reality.

16. A computer-implemented method, comprising:
analyzing, by a computing system operatively coupled to a processor, one or more inputs in form of multispectral videos to track one or more time-series of fluorescence profiles in real-time representative of on-tissue dye dynamics at a section of bodily tissue of interest; and
generating, by the computing system, outputs in form of a mesh representing one or more absorption coefficients at different times and a description of one or more geometric boundaries of the section of bodily tissue, based on the analyzing; and
generating, by the computing system, based on the outputs, a bio-physical model of the section of bodily tissue, wherein the bio-physical model is employable to diagnose one or more medical conditions.

17. The computer-implemented method of claim 16, wherein the one or more inputs comprise one or more multispectral videos captured from one or more medical imaging devices and wherein the one or more time-series of fluorescence profiles represent dye dynamics at the section of bodily tissue.

18. The computer-implemented method of claim 16, further comprising:
analyzing, by the computing system, data from the one or more time-series of fluorescence profiles extracted from one or more multispectral videos describing the on-tissue dye dynamics at the section of bodily tissue; and
estimating, by the computing system, absorption coefficients by employing one or more algorithms to generate a mesh representing absorption geometry based on a time-series of fluorescence intensities of the section of bodily tissue, wherein the generating the bio-physical model is further based on the analyzing the data from the one or more time-series of fluorescence profiles and the estimating.

19. The computer-implemented method of claim 18, wherein the one or more algorithms comprise:
inversion of differential equations wherein observed data, such as the time-series extracted by a time-series extraction component, can be used to invert one or more Diffuse Optical Tomography (DOT) equations such that the inversion can be performed by the processor by selecting values of the absorption coefficients in a DOT equation that best match the observed data.

20. The computer-implemented method of claim 18, further comprising:
assigning, by the computing system, one or more labels indicative of medical information and a confidence score to the section of bodily tissue represented by the bio-physical model, wherein the assigning comprises correlating inputs of patient metadata, labels of medical information, and feature vectors representing on-tissue dye dynamics, and wherein correlation comprises agreement with an internal representation of a feature space learned by a classifier of the computing system such that it can assign one or more labels to one or more feature vectors by choosing labels from memory whose features can be a best match for an unseen example.

21. A system comprising:
a memory; and
a processor that executes computer-executable components stored in the memory, the computer-executable components comprising:
a classification component that:
analyzes a multispectral video having one or more voxels, wherein the multispectral video is generated by a medical imaging device;
generates a classification of bodily tissue that is visible or invisible in the multispectral video generated by the medical imaging device, wherein the classification is provided for the one or more voxels, and wherein the classification also comprises a value indicating a confidence that the classification is accurate as applied to the one or more voxels; and
identifies, based on the classification, similarities in conditions represented by the bodily tissue and characteristics of conditions defined by reference inputs.

22. The system of claim 21, wherein the computer-executable components further comprise:
a display component that overlays the classification over a live stream of the multispectral video in an augmented reality view, wherein the augmented reality view can comprise assigning a color corresponding to one or more labels assigned to a section of bodily tissue during the classification.

23. The system of claim 22, wherein the system also analyzes spatially-distributed time-series of fluorescence data and wherein the computer-executable components further comprise:
an absorption coefficient estimation component that estimates one or more absorption coefficients in three dimensions of one or more physical model structures describing dynamics of the spatially-distributed time-series fluorescence data.

\* \* \* \* \*